(12) United States Patent
Pusey et al.

(10) Patent No.: US 11,883,171 B2
(45) Date of Patent: *Jan. 30, 2024

(54) LATCH MECHANISM FOR PREVENTING LANCET OSCILLATION IN A LANCING DEVICE

(71) Applicant: FACET TECHNOLOGIES, LLC, Atlanta, GA (US)

(72) Inventors: Lauren R. Pusey, Woodstock, GA (US); Greg Lamps, Smyrna, GA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/091,986

(22) Filed: Dec. 30, 2022

(65) Prior Publication Data

US 2023/0144482 A1    May 11, 2023

Related U.S. Application Data

(63) Continuation of application No. 17/741,517, filed on May 11, 2022, now Pat. No. 11,564,603, which is a
(Continued)

(51) Int. Cl.
*A61B 5/151* (2006.01)
*A61B 5/15* (2006.01)

(52) U.S. Cl.
CPC ........ *A61B 5/15194* (2013.01); *A61B 5/1513* (2013.01); *A61B 5/1519* (2013.01);
(Continued)

(58) Field of Classification Search
CPC .......... A61M 2005/208; A61M 5/2033; A61B 5/150022; A61B 5/150412; A61B 5/15113; A61B 5/15194; A61B 5/15117; A61B 5/1519; A61B 5/150183; A61B 5/1513; A61B 5/150503; A61B 5/150519; A61B 5/15144; A61B 5/15186; A61B 5/1411
See application file for complete search history.

(56) References Cited

U.S. PATENT DOCUMENTS

| 4,203,446 A | 5/1980 | Hofert et al. |
| 4,841,985 A | 6/1989 | Wanamaker |

(Continued)

FOREIGN PATENT DOCUMENTS

| EP | 0898936 A2 | 3/1999 |
| EP | 1074219 A2 | 2/2001 |

(Continued)

OTHER PUBLICATIONS

International Search Report & Written Opinion for PCT/US2012/060847; dated Jan. 23, 2013; 11 pgs.

*Primary Examiner* — Katherine M Shi

(57) ABSTRACT

A lancing device including a latch that pivots between a non-blocking position allowing a lancet carrier and a lancet to advance and retract through a first forward and reverse lancing stroke and a blocking position preventing further/excess/secondary oscillation of the lancet carrier and lancet. The pivotal latch can pivot about an axis perpendicular (e.g., for an L-shaped latch) or parallel/coaxial (e.g., for a sleeve latch) to the advancement and retraction motion of the lancet carrier and lancet.

12 Claims, 20 Drawing Sheets

Related U.S. Application Data continuation of application No. 17/034,888, filed on Sep. 28, 2020, now abandoned, which is a continuation of application No. 15/824,443, filed on Nov. 28, 2017, now Pat. No. 10,820,849, which is a continuation of application No. 13/655,168, filed on Oct. 18, 2012, now Pat. No. 9,844,331.

(60) Provisional application No. 61/570,894, filed on Dec. 15, 2011.

(52) U.S. Cl.
CPC .. *A61B 5/150022* (2013.01); *A61B 5/150106* (2013.01); *A61B 5/15113* (2013.01); *A61B 5/15117* (2013.01); *A61B 5/150183* (2013.01); *A61B 5/150412* (2013.01); *A61B 5/150519* (2013.01); *A61B 5/15144* (2013.01); *A61B 5/15146* (2013.01); *A61B 5/150946* (2013.01)

(56) References Cited

U.S. PATENT DOCUMENTS

| | | |
|---|---|---|
| 4,895,147 A | 1/1990 | Bodicky et al. |
| 4,924,879 A | 5/1990 | O'Brien |
| 4,976,724 A | 12/1990 | Nieto et al. |
| 5,196,025 A | 3/1993 | Ranalletta et al. |
| D342,573 S | 12/1993 | Cerola |
| 5,282,822 A | 2/1994 | Macors et al. |
| 5,318,584 A | 6/1994 | Lange et al. |
| 5,423,847 A | 6/1995 | Strong et al. |
| 5,464,418 A | 11/1995 | Schraga |
| 5,518,004 A | 5/1996 | Schraga |
| 5,554,166 A | 9/1996 | Lange et al. |
| 5,613,978 A | 3/1997 | Harding |
| D379,516 S | 5/1997 | Rutter |
| 5,730,753 A | 3/1998 | Morita |
| RE35,803 E | 5/1998 | Lange et al. |
| 5,916,230 A | 6/1999 | Brenneman et al. |
| 5,951,493 A | 9/1999 | Douglas et al. |
| 5,954,738 A | 9/1999 | LeVaughn et al. |
| 5,984,940 A | 11/1999 | Davis et al. |
| 6,022,366 A | 2/2000 | Schraga |
| 6,045,567 A | 4/2000 | Taylor et al. |
| D428,150 S | 7/2000 | Ruf et al. |
| 6,156,050 A | 12/2000 | Davis et al. |
| 6,156,051 A | 12/2000 | Schraga |
| 6,168,606 B1 | 1/2001 | Levin et al. |
| 6,197,040 B1 | 3/2001 | LeVaughn et al. |
| D444,557 S | 7/2001 | Levaughn et al. |
| D447,566 S | 9/2001 | Levaughn et al. |
| 6,283,982 B1 | 9/2001 | Levaughn et al. |
| 6,322,575 B1 | 11/2001 | Schraga |
| 6,332,871 B1 | 12/2001 | Douglas et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,514,270 B1 | 2/2003 | Schraga |
| 6,530,937 B1 | 3/2003 | Schraga |
| 6,558,402 B1 | 5/2003 | Chelak et al. |
| 6,575,939 B1 | 6/2003 | Brunel |
| 6,602,268 B2 | 8/2003 | Kuhr et al. |
| 6,645,219 B2 | 11/2003 | Roe |
| 6,749,618 B2 | 6/2004 | Levaughn et al. |
| D493,532 S | 7/2004 | Levaughn et al. |
| 6,811,557 B2 | 11/2004 | Schraga |
| 6,858,015 B2 | 2/2005 | List |
| 6,887,253 B2 | 5/2005 | Schraga |
| 6,929,650 B2 | 8/2005 | Fukuzawa et al. |
| 6,986,777 B2 | 1/2006 | Kim |
| 7,105,006 B2 | 9/2006 | Shraga |
| D530,424 S | 10/2006 | Manser et al. |
| 7,150,755 B2 | 12/2006 | Levaughn et al. |
| 7,175,641 B1 | 2/2007 | Schraga |
| 7,223,276 B2 | 5/2007 | List et al. |
| 7,273,484 B2 | 9/2007 | Thoes et al. |
| 7,288,102 B2 | 10/2007 | Griffin et al. |
| 7,311,718 B2 | 12/2007 | Schraga |
| D560,805 S | 1/2008 | Young et al. |
| 7,322,998 B2 | 1/2008 | Kuhr et al. |
| D569,975 S | 5/2008 | Wilkinson |
| 7,438,694 B2 | 10/2008 | Boozer et al. |
| D581,533 S | 11/2008 | Ruf et al. |
| D586,465 S | 2/2009 | Faulkner et al. |
| D586,916 S | 2/2009 | Faulkner et al. |
| 7,494,498 B2 | 2/2009 | Lipoma et al. |
| 7,510,564 B2 | 3/2009 | Mace |
| 7,621,931 B2 | 11/2009 | Shraga |
| 7,651,512 B2 | 1/2010 | Chelak et al. |
| 7,655,019 B2 | 2/2010 | LeVaughn et al. |
| D612,051 S | 3/2010 | Ruf |
| 7,674,232 B2 | 3/2010 | Boecker et al. |
| 7,678,126 B2 | 3/2010 | Schraga |
| 7,678,127 B2 | 3/2010 | Trissel et al. |
| 7,682,318 B2 | 3/2010 | Alden et al. |
| 7,780,610 B2 | 8/2010 | Sonoda et al. |
| 7,833,170 B2 | 11/2010 | Matsumoto et al. |
| 7,842,060 B2 | 11/2010 | List |
| 7,867,244 B2 | 1/2011 | Lathrop et al. |
| 7,905,898 B2 | 3/2011 | Schraga |
| 7,909,842 B2 | 3/2011 | Flynn et al. |
| 7,914,547 B2 | 3/2011 | Curry et al. |
| 7,947,057 B2 | 5/2011 | Schraga |
| 7,955,348 B2 | 6/2011 | Trissel et al. |
| 7,998,161 B2 | 8/2011 | Shi |
| 8,016,847 B2 | 9/2011 | Koike et al. |
| 8,016,848 B2 | 9/2011 | Athrop et al. |
| 8,043,318 B2 | 10/2011 | Schraga |
| 8,048,097 B2 | 11/2011 | Schraga |
| 8,048,098 B2 | 11/2011 | Creaven |
| 8,062,268 B2 | 11/2011 | Ratjen |
| 8,105,347 B2 | 1/2012 | Schraga |
| 8,142,466 B2 | 3/2012 | Lipoma et al. |
| 8,152,740 B2 | 4/2012 | Thoes et al. |
| 8,211,036 B2 | 7/2012 | Schraga |
| 8,257,380 B2 | 9/2012 | Schraga |
| 8,267,950 B2 | 9/2012 | Robbins et al. |
| 8,357,107 B2 | 1/2013 | Draudt et al. |
| 8,366,729 B2 | 2/2013 | Levaughn et al. |
| 8,388,639 B2 | 3/2013 | Nicholls et al. |
| 8,398,664 B2 | 3/2013 | Lamps et al. |
| 8,469,986 B2 | 6/2013 | Schraga |
| 8,709,032 B2 | 4/2014 | Schraga |
| 8,932,313 B2 | 1/2015 | Weiss et al. |
| 8,971,982 B2 | 3/2015 | Schraga |
| 9,055,899 B2 | 6/2015 | Lamps et al. |
| 9,095,293 B2 | 8/2015 | Lamps et al. |
| 9,282,918 B2 | 3/2016 | Schraga |
| 9,289,161 B2 | 3/2016 | Schraga |
| 2003/0212344 A1 | 11/2003 | Yuzhakov et al. |
| 2004/0039302 A1 | 2/2004 | Kim |
| 2004/0162573 A1 | 8/2004 | Kheiri |
| 2004/0249405 A1 | 12/2004 | Watanabe et al. |
| 2004/0254599 A1 | 12/2004 | Lipoma et al. |
| 2005/0085840 A1 | 4/2005 | Yi et al. |
| 2005/0125017 A1 | 6/2005 | Kudrna et al. |
| 2005/0125019 A1 | 6/2005 | Kudrna et al. |
| 2005/0143771 A1 | 6/2005 | Stout et al. |
| 2005/0159768 A1 | 7/2005 | Boehm et al. |
| 2005/0234492 A1 | 10/2005 | Tsai et al. |
| 2005/0234495 A1 | 10/2005 | Schraga |
| 2006/0100655 A1 | 5/2006 | Leong et al. |
| 2006/0100656 A1 | 5/2006 | Olson et al. |
| 2006/0224172 A1 | 10/2006 | LeVaughn et al. |
| 2006/0247671 A1 | 11/2006 | LeVaughn |
| 2006/0264996 A1 | 11/2006 | LeVaughn et al. |
| 2007/0055298 A1 | 3/2007 | Uehata et al. |
| 2007/0083222 A1 | 4/2007 | Schraga |
| 2007/0100364 A1 | 5/2007 | Sansom |
| 2007/0173874 A1 | 7/2007 | Uschold et al. |
| 2007/0173875 A1 | 7/2007 | Uschold |
| 2008/0082117 A1 | 4/2008 | Ruf |
| 2008/0146966 A1 | 6/2008 | Levaughn et al. |
| 2008/0147108 A1 | 6/2008 | Kennedy |

(56) References Cited

U.S. PATENT DOCUMENTS

| | | |
|---|---|---|
| 2008/0255598 A1 | 10/2008 | LeVaughn et al. |
| 2009/0030441 A1 | 1/2009 | Kudrna et al. |
| 2010/0160942 A1 | 6/2010 | Amp et al. |
| 2010/0160943 A1 | 6/2010 | Lamp et al. |
| 2010/0234870 A1 | 9/2010 | Ruf |
| 2013/0158586 A1 | 6/2013 | Pusey et al. |

FOREIGN PATENT DOCUMENTS

| | | |
|---|---|---|
| EP | 1163879 A2 | 12/2001 |
| EP | 1779781 A2 | 5/2007 |
| WO | 9704707 A1 | 2/1997 |
| WO | 0128423 A2 | 4/2001 |
| WO | 2006031535 A2 | 3/2006 |
| WO | 2007130830 A2 | 11/2007 |
| WO | 2007146913 A2 | 12/2007 |
| WO | 2010080584 A1 | 7/2010 |
| WO | 2010080585 A1 | 7/2010 |
| WO | 2011050142 A1 | 4/2011 |

LATCH MECHANISM FOR PREVENTING LANCET OSCILLATION IN A LANCING DEVICE

CROSS-REFERENCE TO RELATED APPLICATION

This application is a continuation of U.S. Non-Provisional patent application Ser. No. 17/741,517 filed May 11, 2022, which is a continuation of U.S. Non-Provisional patent application Ser. No. 17/034,888 filed Sep. 28, 2020, which is a continuation of U.S. Non-Provisional patent application Ser. No. 15/824,443 filed Nov. 28, 2017, now U.S. Pat. No. 10,820,849 issued Nov. 3, 2020, which is a continuation of U.S. Non-Provisional patent application Ser. No. 13/655,168 filed Oct. 18, 2012, now U.S. Pat. No. 9,844,331 issued Dec. 19, 2017, which claims the priority benefit of U.S. Provisional Patent Application Ser. No. 61/570,894 filed Dec. 15, 2011, the entireties of which are hereby incorporated herein by reference for all purposes.

TECHNICAL FIELD

The present invention relates generally to the field of medical devices, and more particularly to a lancing device for blood sampling and testing with an incorporated mechanism for preventing excess lancet oscillation.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism with a drive spring, a charging mechanism for energizing the spring, and a release mechanism for releasing the drive mechanism to propel a lancet through a lancing stroke. A lancet is propelled by the drive mechanism from a retracted position within the housing to an extended position where a sharp tip portion of the lancet projects from the housing to prick the subject's skin at a desired lancing site. U.S. Patent App. Pub. No. US2011/0196261 and U.S. Patent App. Pub. No. US2010/0160942 show example lancing devices and are incorporated herein by reference.

Many known lancing devices include two springs, a drive spring to drive the lancet along an advancing portion of the lancet stroke toward the lancing site, and a return spring to retract the lancet along a return portion of the lancet stroke back into the housing. Achieving the correct balance of spring forces between the two springs presents design challenges, and incorrect balance can reduce the lancet speed, potentially increasing pain sensation. It has also been discovered that some drive mechanisms can cause or permit the lancet to continue to oscillate after the lancing stroke (one forward and reverse cycle) is completed, possibly pricking the subject's skin unintentionally a second time or more and resulting in a greater sensation of pain for the patient. Friction between device components and/or energy dissipation from the lancing of the skin serves to dampen lancet oscillation in previously known lancing devices to some extent, but not to an entirely effective extent.

Thus it can be seen that needs exist for the reduction or elimination of excess lancet oscillation in a lancing device. It is to the provision of a system and method for preventing excess lancet oscillation in a lancing device meeting these and other needs that the present invention is primarily directed.

SUMMARY

The present invention relates to systems and methods for preventing excess lancet oscillation in lancing devices. In example embodiments, a latch mechanism allows operation of the drive mechanism to carry out the lancing stroke unimpeded, but after a single penetration of the skin at the lancing site the latch is engaged to reduce or prevent further oscillation of the lancet, to thereby prevent the lancet from contacting the skin a second time. In multi-use designs, the latch mechanism optionally also holds the drive mechanism during ejection of the lancet from the drive mechanism.

In one aspect, the present invention relates to a lancing device including a drive mechanism for advancing and retracting a lancet through a lancing stroke, and a latch mechanism for allowing advancement and retraction of the lancet once (through the lancing stroke) but limiting further/excess/secondary oscillation thereof. In one embodiment, the latch mechanism includes a pivotal L-shaped latch member having a leg, a foot extending generally perpendicular to and transversely offset from the leg, and a resilient finger extending generally parallel to and transversely offset from the leg and operably engaged and deflected by a ramp. In another embodiment, the latch mechanism includes a pivotal (rotary) tube/sleeve-shaped latch member with an angled guide surface and with an axially extending tooth having a lancet carrier stop projecting transversely therefrom for operable engagement by a resilient finger.

In another aspect, the invention relates to a method of preventing secondary oscillation of a lancet in a lancing device. The method comprises providing a lancing device with a pivotal latch mechanism configured and positioned to permit a first oscillation of the lancet when the latch mechanism is in a non-blocking position, and moving the latch mechanism to a blocking position where subsequent/excess oscillations are prevented.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are exemplary and explanatory of preferred embodiments of the invention, and are not restrictive of the invention, as claimed.

DETAILED DESCRIPTION OF EXAMPLE EMBODIMENTS

Figure 1A:
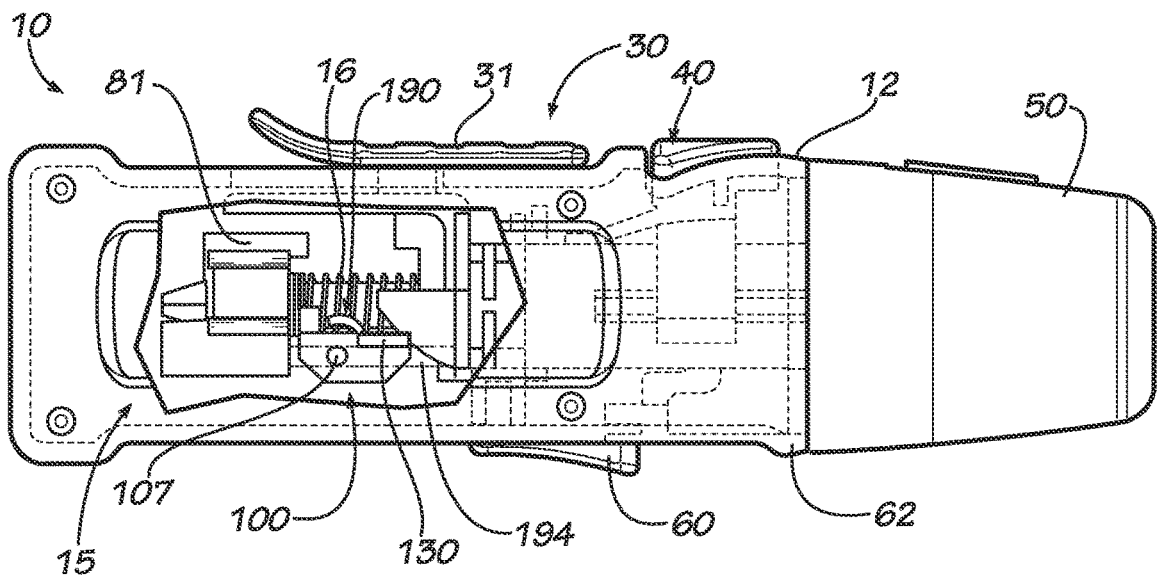
FIG. 1A is a side view of a lancing device according to a first example embodiment of the present invention, with a portion of the housing removed to show internal components of the device, showing a latch mechanism for preventing excess lancet oscillation, with the latch in a blocking position.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1A-5 show a lancing device 10 according to a first example embodiment of the invention. The lancing device 10 generally includes a drive mechanism 15, a charging mechanism 30, a release mechanism 40, and a housing 12 at least partially enclosing these components.

The drive mechanism 15 includes a drive spring 14 and a return spring 16 for driving a lancet carrier 18 through a lancing stroke. In multi-use embodiments such as that depicted, the lancet carrier 18 removably engages a lancet 20 comprising a lancet body with a sharp lancet tip 22 projecting therefrom. The charging mechanism 30 operates to retract the lancet carrier 18 from a neutral or normal position to a retracted or charged position to energize the drive spring 14, and the release mechanism 40 holds the lancet carrier 18 in the retracted position and upon actuation releases the lancet carrier 18 to initiate the lancing stroke. The charged drive spring 14 propels the lancet carrier 18 and lancet 20 along an advancing/forward portion of the lancing stroke, from the charged position within the housing to an advanced/extended position where at least the sharp lancet tip 22 projects from the housing 12 to penetrate the subject's skin at a lancing site. The forward portion of the lancing stroke charges the return spring 16, and the now-charged return spring then returns the lancet carrier 18 and lancet 20 to the neutral/normal position.

Optionally, the housing can include an endcap or nosecone portion 50 that provides for adjustment of the penetration depth of the lancet tip 22. Removal of the endcap 50 also allows access for removal and replacement of the disposal lancet 20 after use, for example, by actuation of a lancet ejection mechanism 60, in some multi-use designs.

In other embodiments, the lancing device 10 includes other conventional drive mechanisms, charging mechanisms, release mechanisms, and/or depth-adjustment mechanisms. For example, the drive mechanism can include a single spring element for driving and retracting, the charging mechanism can be provided by a twist-to-charge or push-to-charge mechanism, the release mechanism can be provided by a slide or rotary release, and/or the lancing device can include a multi-lancet carrier holding a plurality of lancets for sequential use.

In the depicted embodiment, the lancet carrier 18 and the lancet 20 are separates parts, with the lancet being replaceable so that the lancing device 10 can be used multiple times. In disposable embodiments, the lancet carrier/holder and the lancet are a single integral component. And in the depicted embodiment, a spring retainer 80 for the drive spring 14 and/or return spring 16 is mounted onto and travels with the lancet carrier 18, and is such considered to be a component of the lancet carrier, even though it could additionally or alternatively be considered to be a component of the drive mechanism. As such, reference herein (including the appended claims) to the lancet carrier 18 is intended to also refer to the lancet 20 itself as well as to any component of the drive mechanism 15 or another mechanism of the lancing device 10 that travels with the lancet carrier.

The lancing device 10 of the first embodiment further includes a latch mechanism 100 that functions to permit a first oscillation of the lancet carrier 18 and lancet 20 then prevent subsequent (i.e., excess or secondary) oscillations. The term "oscillation" as used herein is defined as the lancet 20 generally moving from a first/retracted position forward to a second/extended position (i.e., where the lancet tip 22 projects out of the housing 12 to contact the lancing site), and rearward back to or at least toward the first/retracted position (i.e., such that the lancet tip is retracted back into the housing).

Figure 1B:
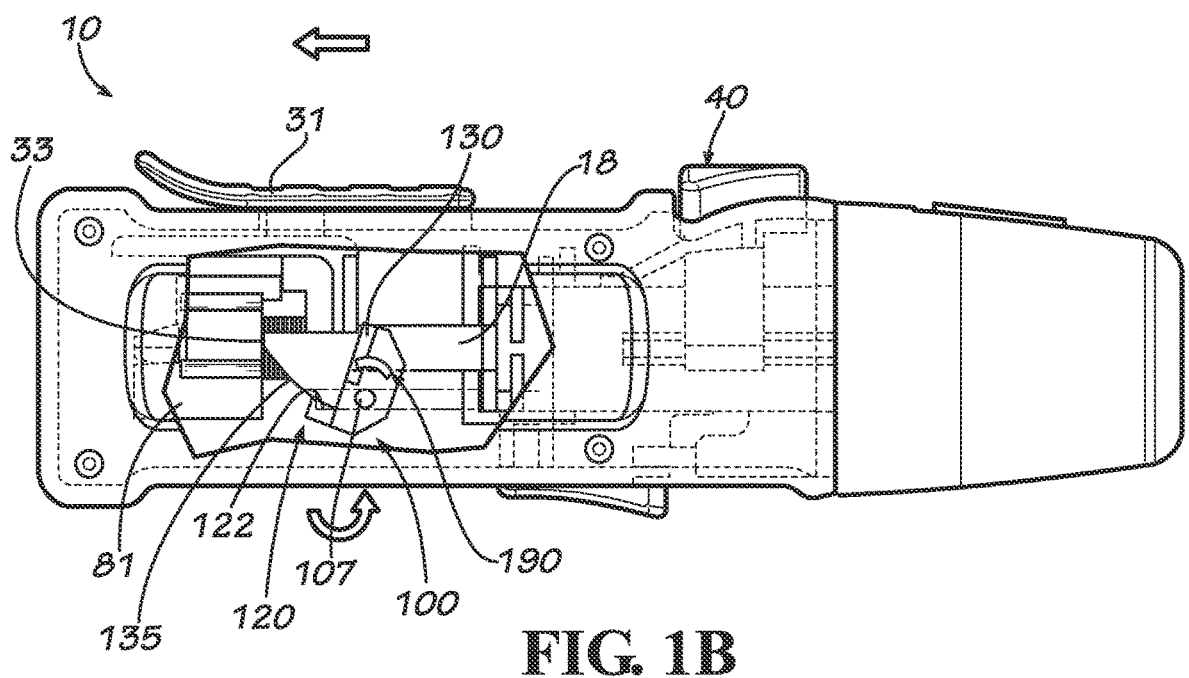
FIG. 1B shows the lancing device of FIG. 1A with the drive mechanism being charged and the latch being pivoted toward an intermediate non-blocking position.
Figure 1C:
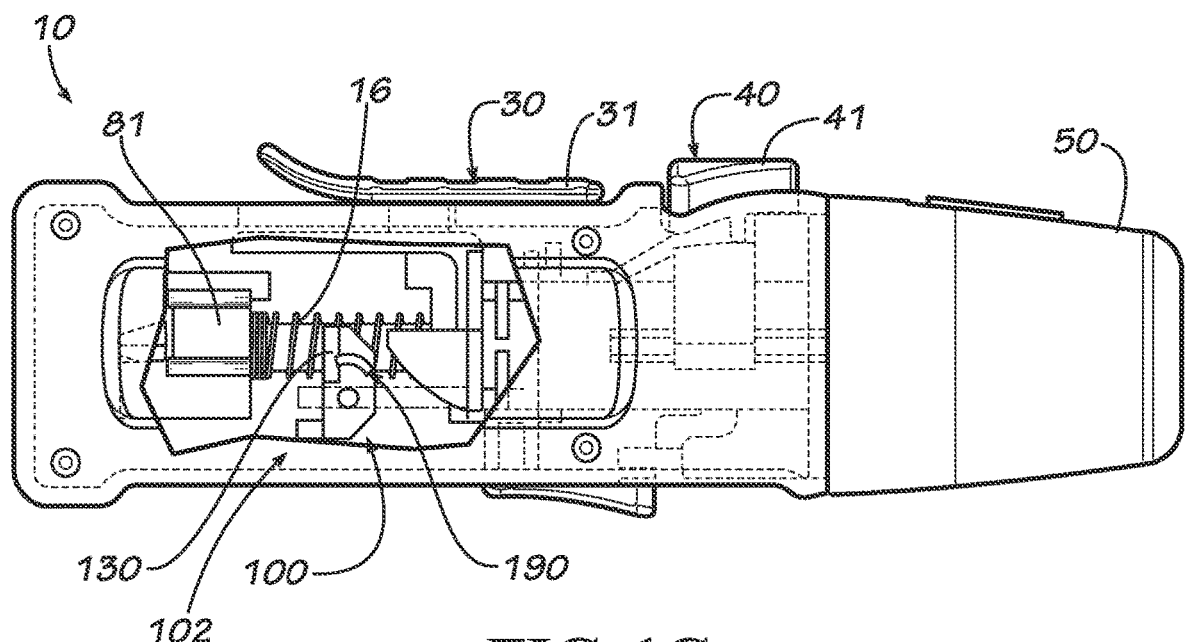
FIG. 1C shows the lancing device of FIG. 1B with the latch in the intermediate non-blocking position.
Figure 1D:
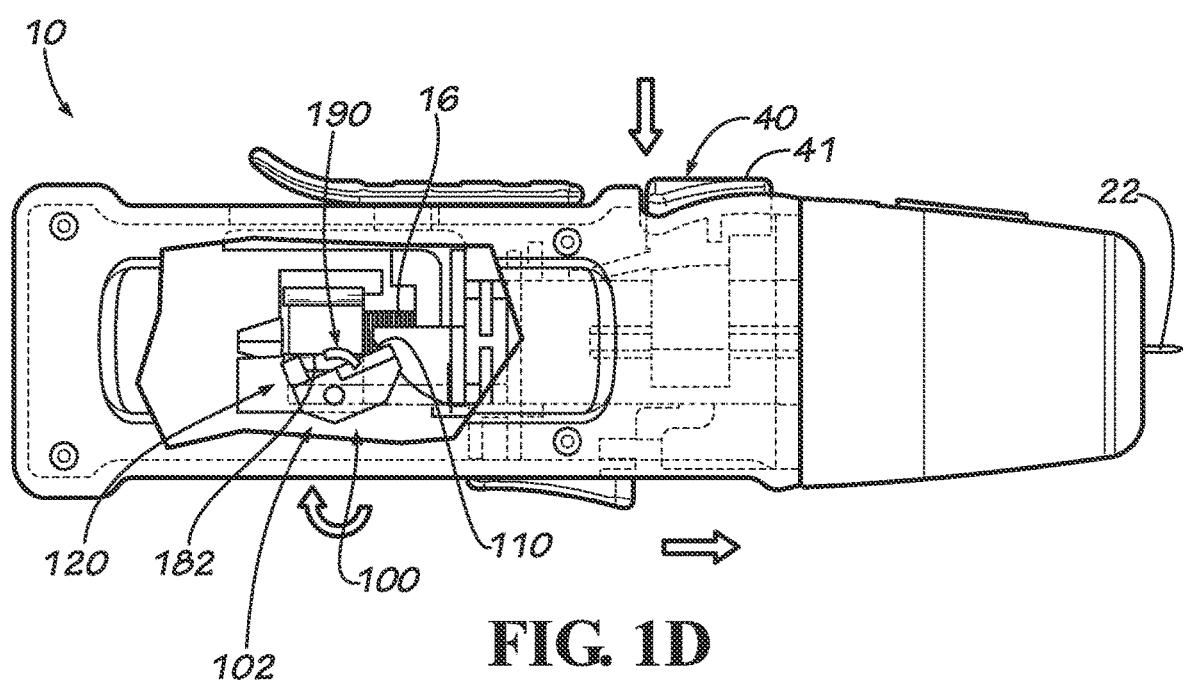
FIG. 1D shows the lancing device of FIG. 1C with the lancet traveling along a forward portion of its lancing stroke and the latch pivoted to a press non-blocking position.
Figure 1E:
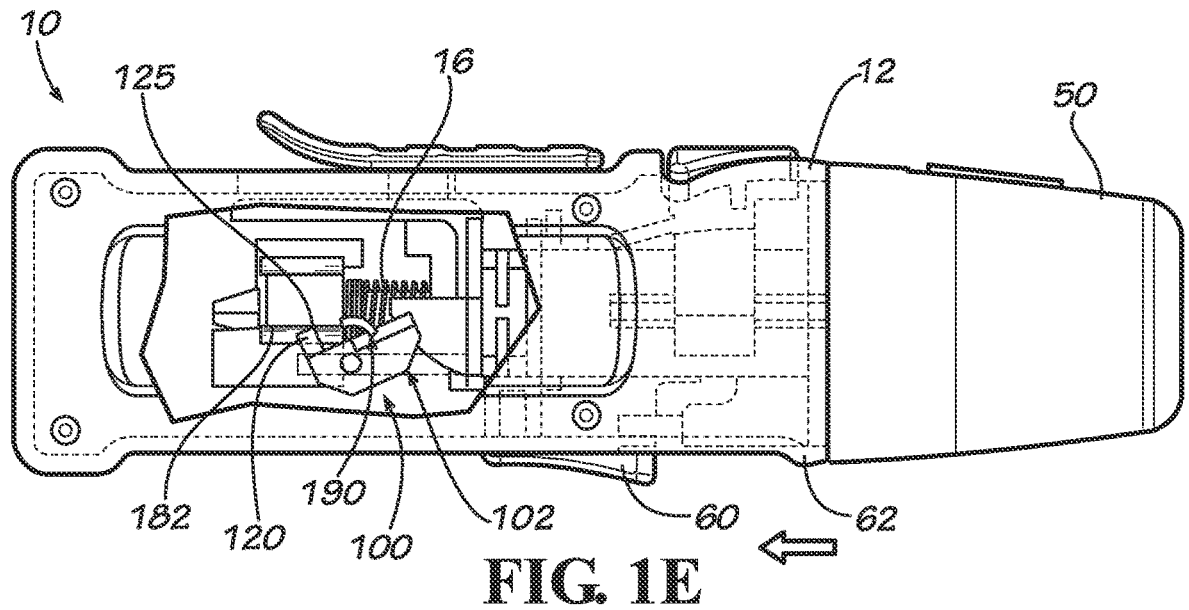
FIG. 1E shows the lancing device of FIG. 1D with the lancet traveling along a rearward return portion of its lancing stroke and the latch retained in the press non-blocking position.
Figure 1F:
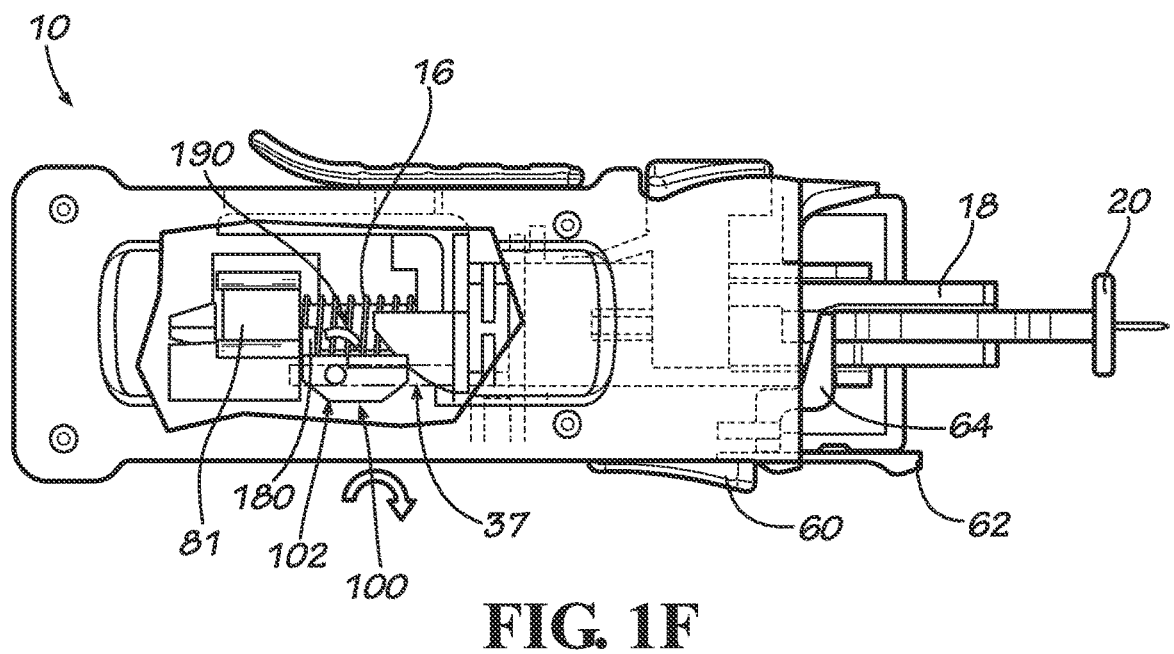
FIG. 1F shows the lancing device of FIG. 1E with the lancet traveling farther along its rearward return portion of its lancing stroke and the latch pivoted back to the blocking position of FIG. 1A.
Figure 2A:
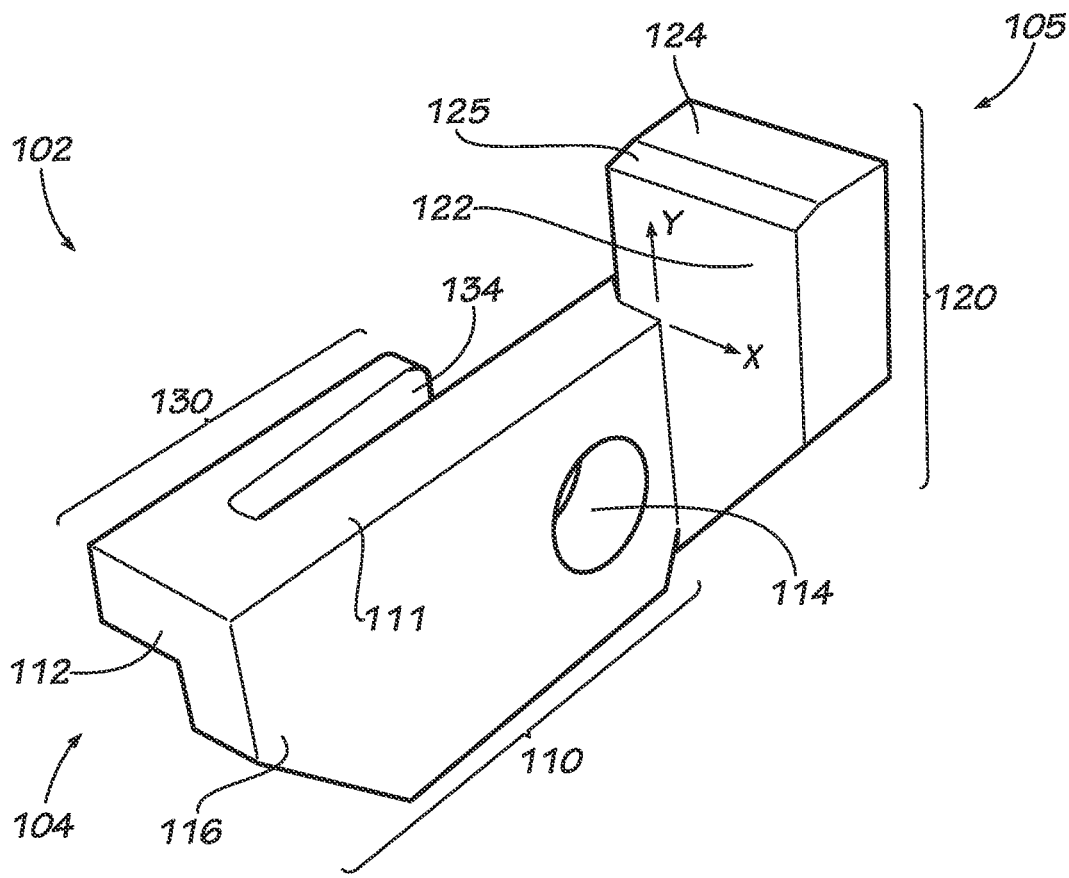
FIG. 2A is a front perspective view of the latch member of the latch mechanism of FIGS. 1A-1F.
Figure 2B:
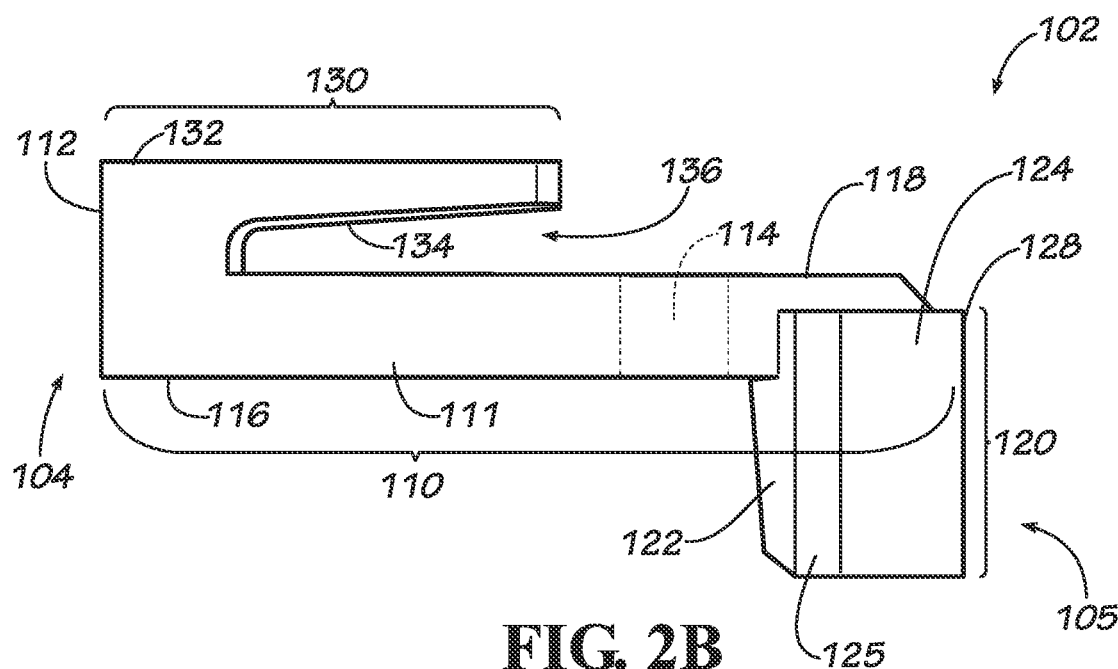
FIG. 2B is a top view of the latch member of the latch mechanism of FIGS. 1A-1F.
Figure 2C:
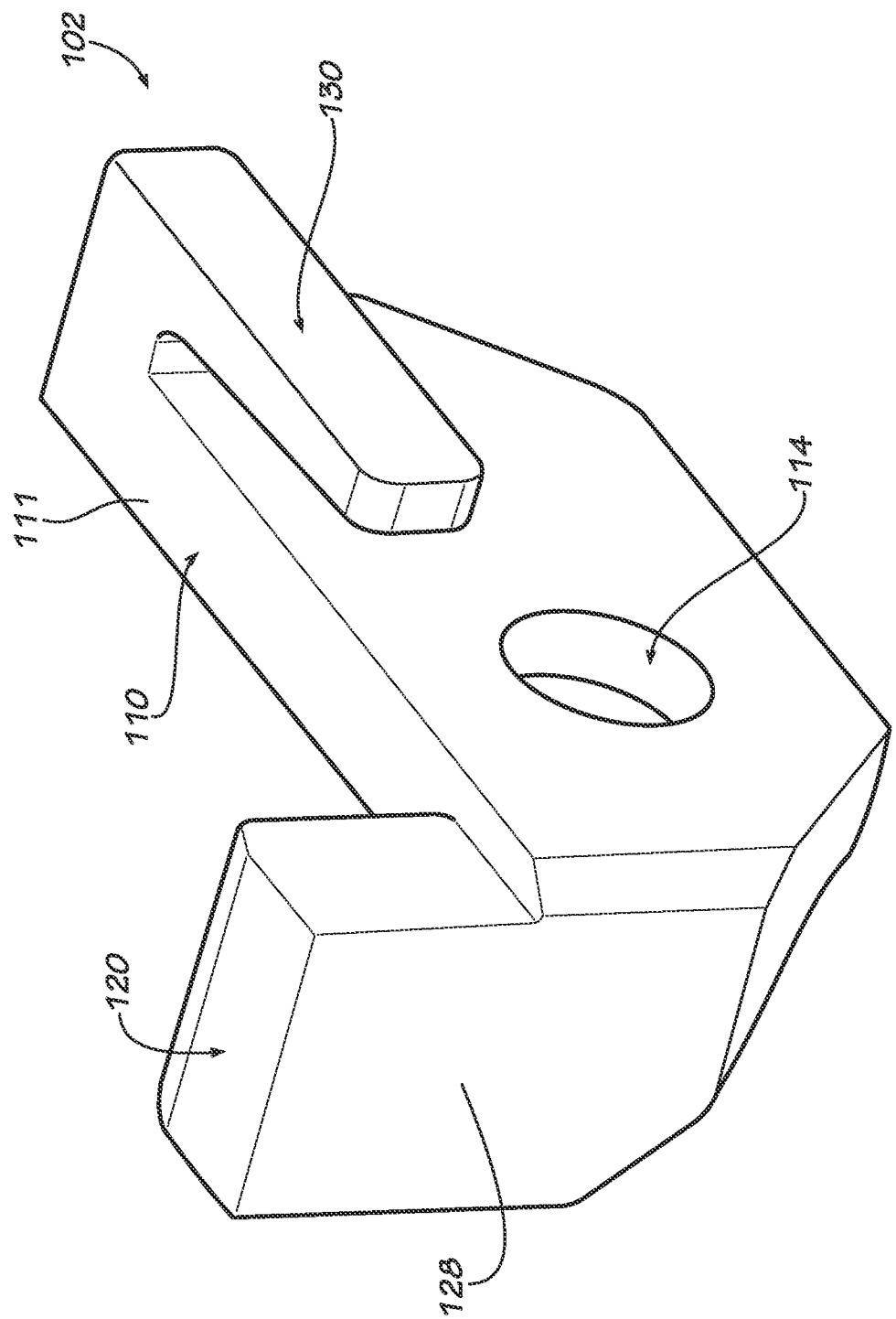
FIG. 2C is a rear perspective view of the latch member of the latch mechanism of FIGS. 1A-1F.
Figure 3A:
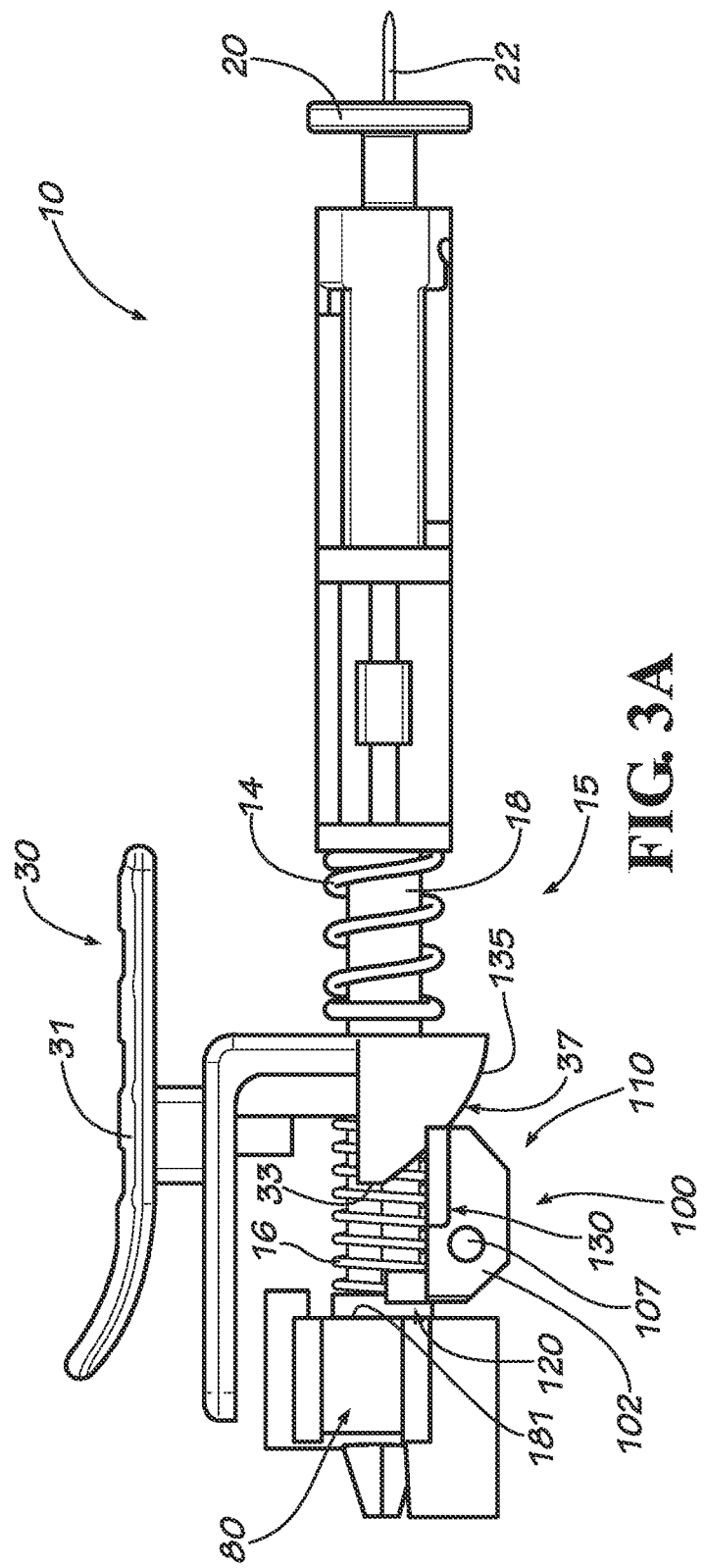
FIG. 3A shows the lancing device of FIG. 1A with the housing entirely removed to show details of internal components of the latch, charge, and drive mechanisms, with the latch mechanism in the blocking position of FIG. 1A.
Figure 3B:
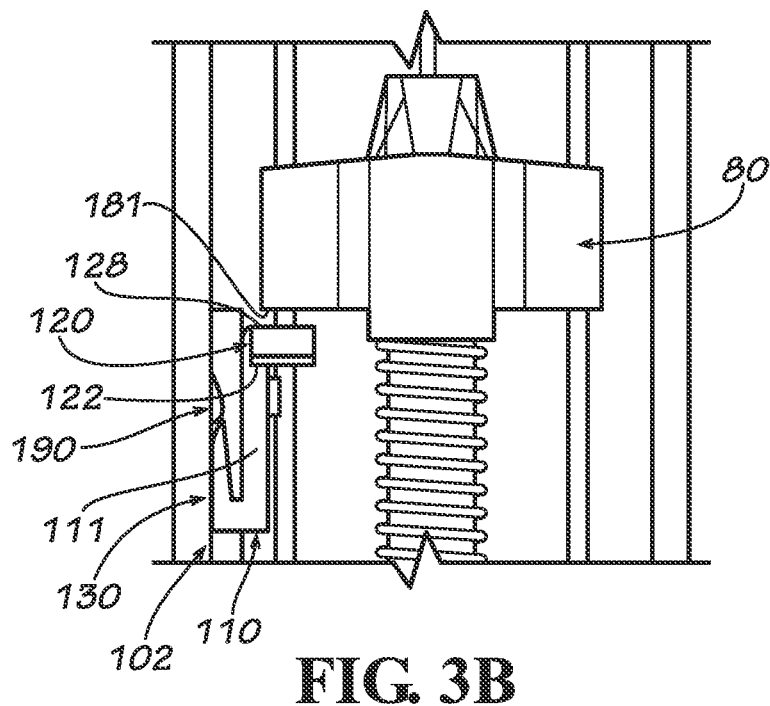
FIG. 3B is a top view of a portion of the lancing device of FIG. 1A with a top portion of the housing removed to show the internal components, with the latch mechanism in the blocking position of FIG. 1A.
Figure 3C:
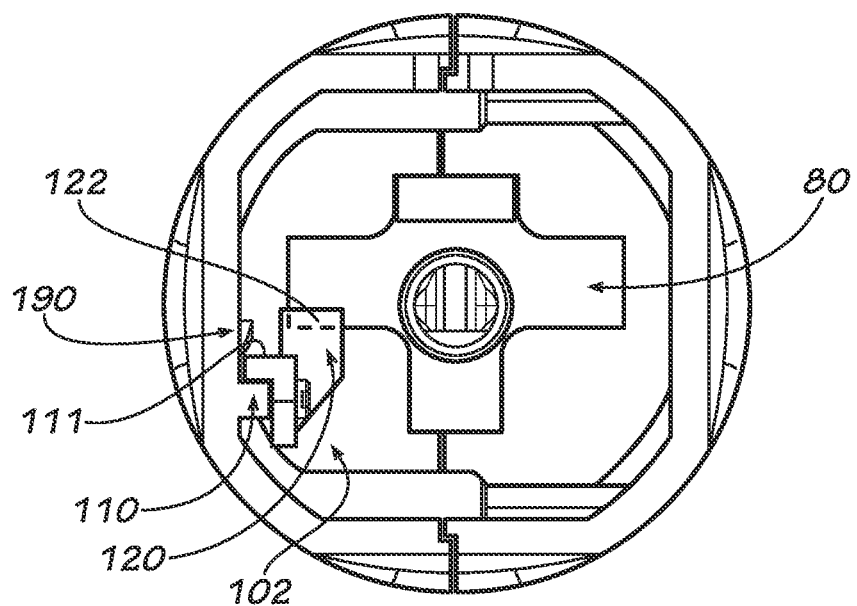
FIG. 3C is a front view of the lancing device of FIG. 1A with a front portion of the housing removed to show the internal components, with the latch mechanism in the blocking position of FIG. 1A.
Figure 3D:
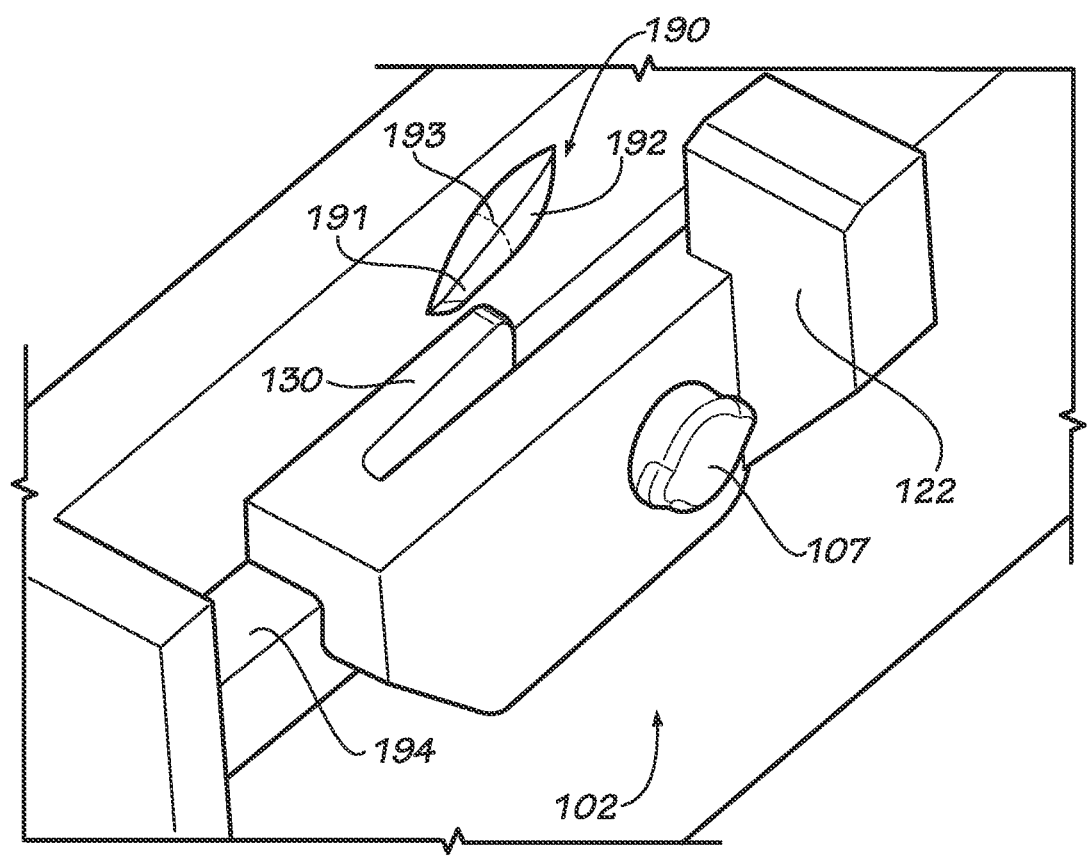
FIG. 3D is a front perspective view of the latch mechanism in the blocking position of FIG. 1A, showing details of a detent ramp of the latch mechanism.
Figure 3E:
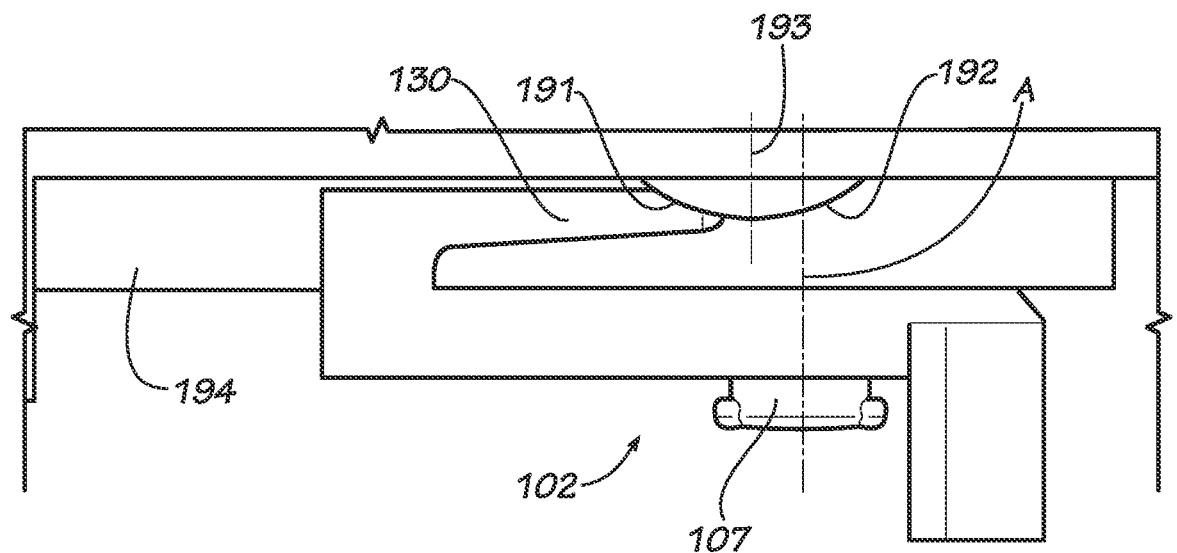
FIG. 3E is a top view of the latch mechanism of FIG. 3D, showing details of the detent ramp of the latch mechanism.
Figure 4:
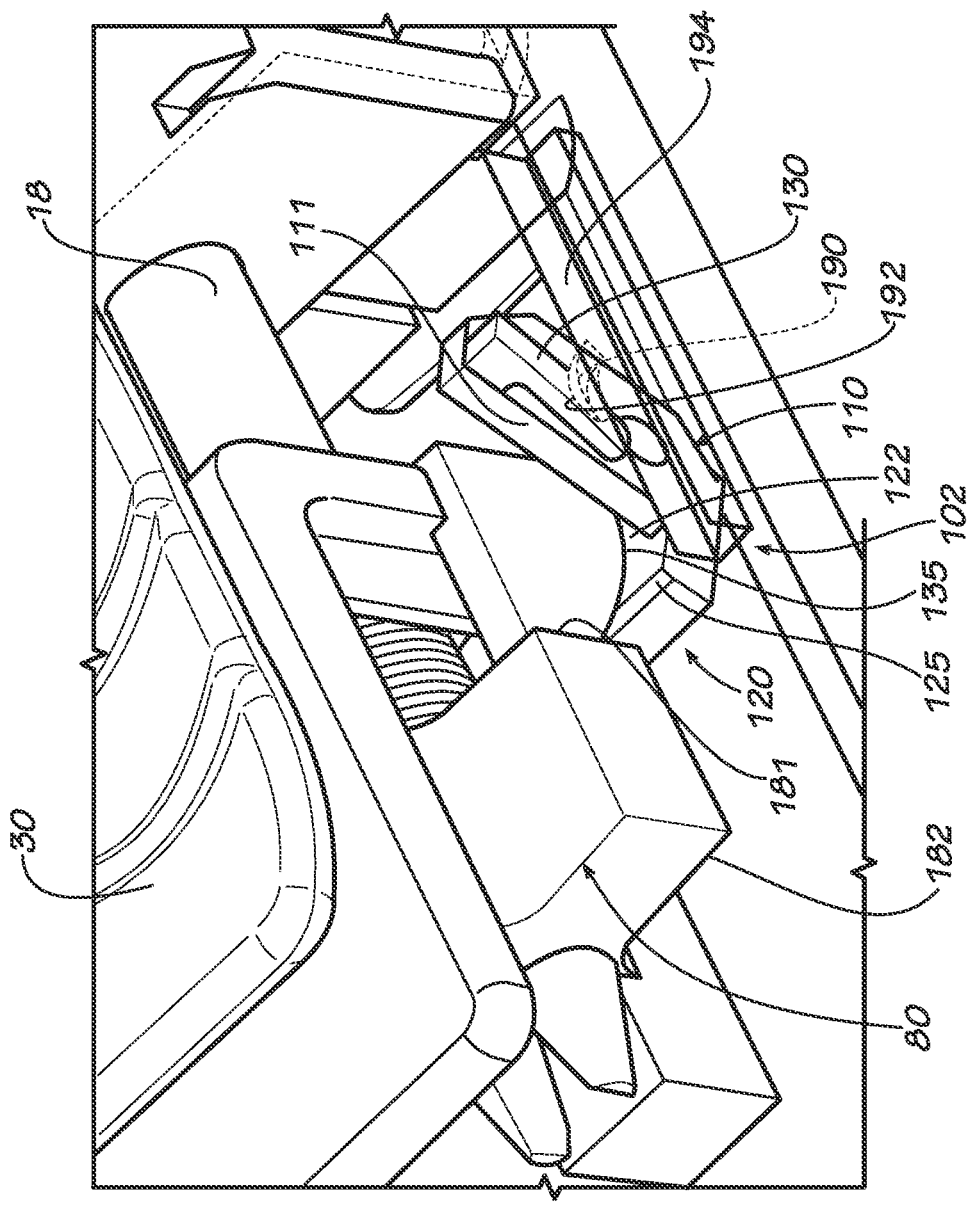
FIG. 4 is a rear perspective view of the latch member and the detent ramp with the latch mechanism in the position of FIG. 1B.
Figure 5:
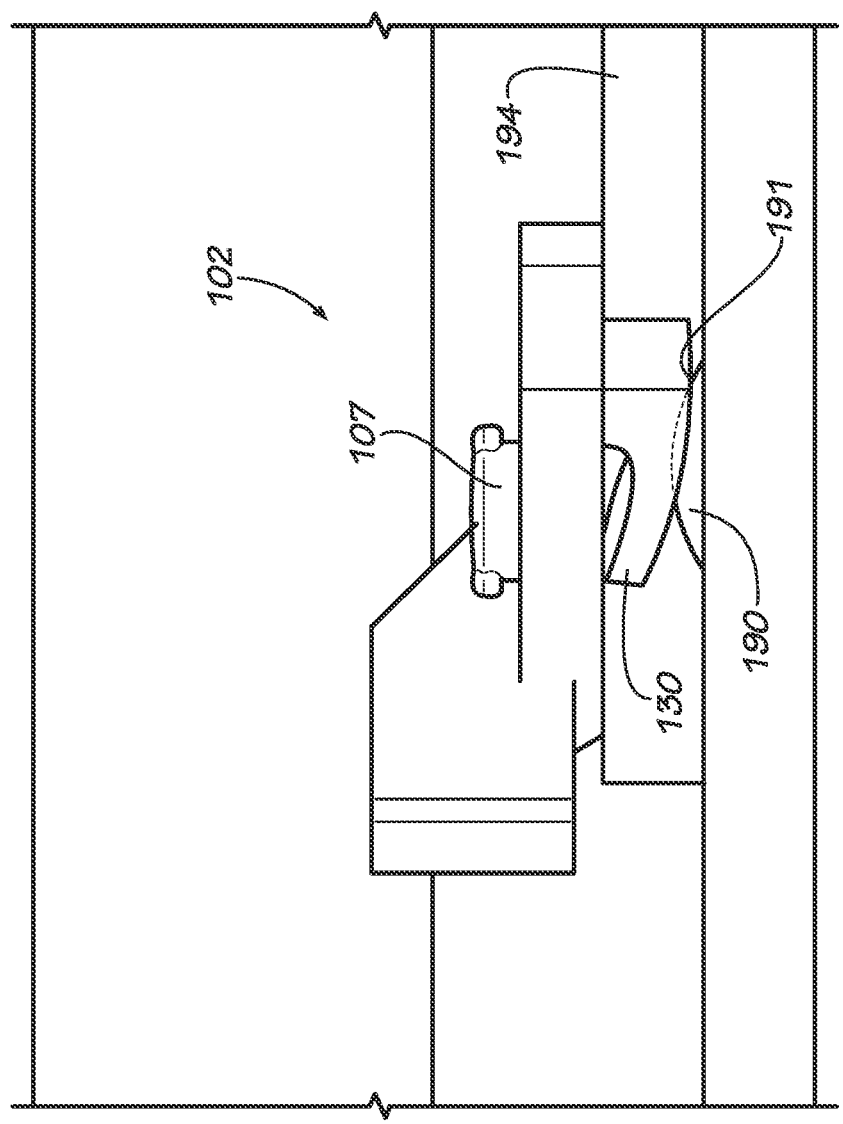
FIG. 5 is a top perspective view of the latch member and the detent ramp with the latch mechanism in the press non-blocking position of FIGS. 1D and 1E.

FIGS. 1A-1F show details and a sequence of operation of the lancing device 10 with the latch mechanism 100, and FIGS. 2A-5 show components of the latch mechanism in greater detail, with FIGS. 3A-3E corresponding to FIGS. 1A and 1F, with FIG. 4 corresponding to FIG. 1B, and FIG. 5 corresponding to FIGS. 1D and 1E. In typical embodiments such as that depicted, the latch mechanism 100 includes a latch member 102, a latch-pivoting element 135 of the charging mechanism 30, a latch-engaging element 181 of the lancet carrier 18, a spring-biased latch retainer 130 of the latch member or other portion of the lancing device 10, and a ramp 190 of the housing 12 or other portion of the lancing device.

The latch member 102 is pivotally coupled to an element of the lancing device 10. For example, the latch member 102 can be pivotally coupled to the housing 12 by a pivot pin 107 with an axis transverse to the angular motion of the latch member 102, as depicted. As used herein, "pivot" (and other terms with that as the root) includes to rotate or otherwise move angularly.

The latch member 102 of the depicted embodiment includes a leg 110 and a foot 120 integrally formed with or attached to the leg and extending at an angle from the leg. In the depicted embodiment, for example, the foot 120 includes at least a portion that extends from the leg 110 in a direction Y that is generally perpendicular to the pivot axis and at least a portion that extends laterally from the leg in a direction X that is generally parallel to the pivot axis. More particularly, the depicted latch member 102 is generally L-shaped with the leg 110 having a first end 104 and a second end 105, and with the foot 120 extending generally perpendicularly and laterally offset from the second end of the leg. The foot 120 includes a charge-pivot face 122 that is engaged by the latch-pivoting element 135 of the charging mechanism 30 during operation, and a drive-stop face 128 that interferes with the latch-engaging element 181 of the drive mechanism 15 during operation to mechanically block excess oscillation. The charge-pivot face 122 and the drive-stop face 128 are formed on the portion of the foot 120 that extends in the X and Y direction from the leg 110 and are oppositely facing away from each other. Typically, the foot 120 includes portions that extend in the opposite of the X and Y directions (that is, across the leg faces referenced as 111 and 116, respectively, in FIG. 2A) for providing strength and durability. In addition, the foot 120 includes an end face 124, and a pressing surface 125 typically defined by a corner chamfer extending between the faces 122 and 128 for pressing engagement against the pressed surface 282 of the lancet carrier 18.

In the depicted embodiment, the spring-biased latch retainer 130 is in the form of a resilient finger 130 that is integrally formed with or attached to the leg 110, the housing 12, or another element of the lancing device 10, and that interacts with a rear portion 192 of a ramp 190 (described below). In typical embodiments, the finger 130 extends from, and is generally parallel to and laterally offset from the leg 110 on the opposite side from the foot 120. In the depicted embodiment, for example, the finger 130 extends from the first end 104 of the leg 110. The finger 130 includes a contact (e.g., outer) face 132 that engages the ramp 190 when the latch 102 is pivoted through its operating motion. In the depicted embodiment, the finger 130 also includes an opposite (e.g., inner) face 134 that cooperates with a face of the leg 110 to define a slit 136. The finger 130 is preferably sufficiently thin and resilient to allow a degree of flexure/deflection toward (as permitted by the slit 136) and away from the leg 110. As such, the resilient finger 130 functions as a spring to provide a biasing force against the ramp 190 when the two components are moved into engagement with each other. In other embodiments, instead of the cantilevered finger depicted, the spring-biased latch retainer is in the form of a leaf spring, detent, or other spring-biased element or mechanism. And in yet other embodiments, the position of the finger 130 and the ramp 190 are switched, with the ramp extending outwardly from the latch member 102 and the finger extending inwardly from the housing 12.

The leg 110 includes a drive-pivot face 111 that is engaged by the latch-engaging element 181 of the drive mechanism 15 during operation. The drive-pivot face 111 of the leg 110 is laterally offset from and angled relative to the charge-pivot face 122 of the foot 120, as discussed above. In addition, the pivotal mounting, and thus the pivot point 107, of the latch member 102 is at the leg 110. In the depicted embodiment, the leg 110 includes a mounting hole 114 for receiving the pivot pin 107 to attach the latch member 102 to the lancing device 10 and allow the latch member to rotate about an axis A (see FIG. 3E) generally perpendicular to the advancement and retraction motion of the lancet carrier 18. In other embodiments, the pivot pin extends from the latch member and is rotationally received in a mounting hole in the housing 12 or other element of the lancing device 10.

The latch-pivoting element 135 of the charging mechanism 30 faces generally rearward and moves axially rearward when the charging actuator 31 is actuated to charge the drive mechanism 15. In the depicted embodiment, for example, the charging mechanism 30 includes an internal member (e.g., the generally wedge-shaped member 37 depicted) extending from the charging actuator 31 and having a surface defining a charging element 33 that engages the drive mechanism 15 to charge the drive spring 14 and also having a surface defining the latch-pivoting element 135. So when the charging actuator 31 is axially retracted, the latch-pivoting element 135 is also axially retracted into contact with the charge-pivot face 122 of the foot 120 to pivot the latch member 102 in a first/rearward direction from a blocking position to an intermediate non-blocking position. The latch-pivoting element 135 is typically ramped, for example it can have an arcuate shape as depicted. Additionally or alternatively, the charge-pivot face 122 of the foot 120 can be ramped, for example arcuate, to induce the latch-pivoting function.

The latch-engaging element 181 of the lancet carrier 18 faces generally forward and moves axially forward with the lancet 20 when the drive mechanism is released/actuated to drive the lancet through the lancing stroke. For example, the drive spring 14 and/or return spring 16 can be held on the lancet carrier 18 by a spring retainer 80 that is mechanically connected to the lancet carrier, with the spring retainer defining the latch-engaging element 181 (see FIG. 3A). In the depicted embodiment, the spring retainer 80 has a forward-facing surface defining the latch-engaging element 181 (and also defining a surface that is engaged by the charging element 33 to charge the drive spring 14). And a pressed surface 182 of the lancet carrier 18 can be formed for example by a bottom surface of the spring retainer 80. In other embodiments, the latch-engaging element is in the form of a tab or other projection that extends from or attaches to the spring retainer or another element of the drive mechanism. In any event, when the release mechanism 40 is actuated (e.g., by depressing the release actuator 41), the lancet carrier 18 is released so it can be propelled by the drive spring 14 through the forward portion of the lancing stroke and at the same time the latch-engaging element 181 is propelled into contact with the drive-pivot face 111 of the leg 110 to pivot the latch member 102 in a second/forward direction from the intermediate non-blocking position back toward the blocking position.

The ramp 190 extends inwardly from the housing 12 or other portion of the device 10. The ramp 190 has a front ramped portion 191 that is engaged by the deflected resilient finger (or another type of spring-biased latch retainer) 130 when the drive mechanism 15 propels the lancet carrier 18 through the drive/forward portion of the lancing stroke to cooperatively induce the latch 102 to pivot to the blocking position. Thus, a latch spring biasing the latch 102 from the press non-blocking position to the blocking position is provided by the resilient finger 130 interacting with the front portion 191 of the ramp 190. That is, the deflected resilient finger 130 is biased to resiliently return to its neutral position, and as it so discharges it biases against the front ramped portion 191. In turn, this biases the latch member 102 (to which the finger 130 is attached) to pivot to the blocking position. So the discharging force exerted by the bias of the deflected finger 130 that is in contact with the front ramped portion 191 overcomes any frictional forces between these components. Similarly, the ramp 190 also includes a rear ramped portion 192 that is engaged by the deflected resilient finger 130 when the charging actuator 31 is axially retracted to cooperatively induce the latch 102 to pivot to and be retained in the intermediate non-blocking position. Thus, the spring-biased latch retainer 130 is provided by the resilient finger interacting with the rear portion 192 of the ramp 190. In this way, the ramp 190 urges the latch 102 to remain in either the blocked or intermediate non-blocked position when the latch is not in contact with the latch-engaging element 181 or the latch-pivoting element 135. In typical embodiments such as that depicted, the ramp 190 is arcuate and elongated, and it includes a tipping point 193 between the front and rear ramped portions 191 and 192.

Figure 6A:
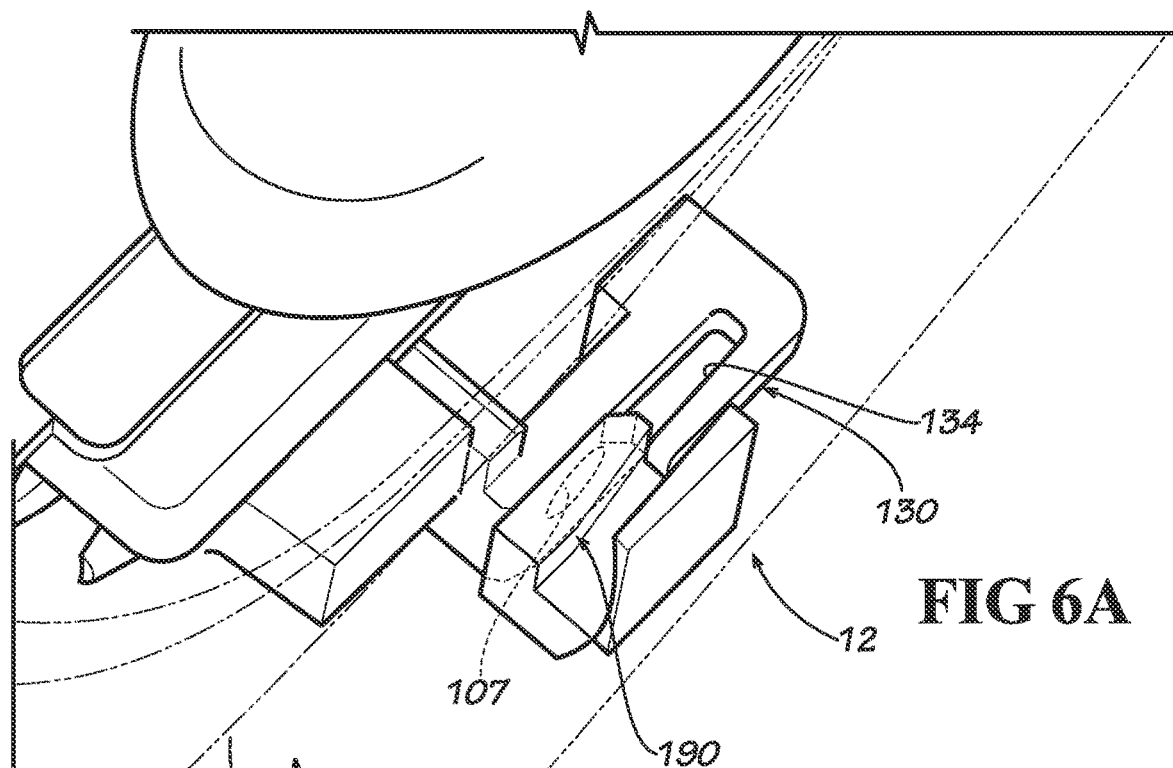
FIG. 6A is perspective view of a portion of a latch mechanism according to an alternative embodiment to that shown in FIGS. 1A-5, with the latch mechanism in the blocking position.
Figure 6B:
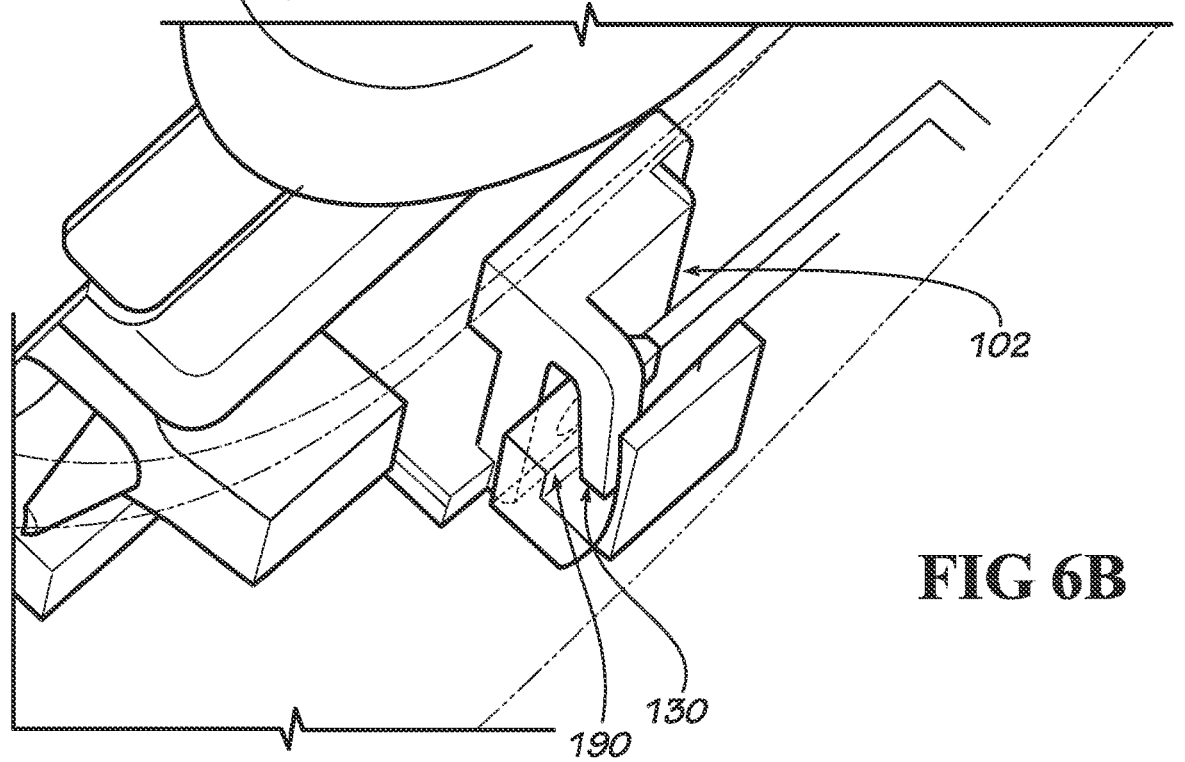
FIG. 6B shows the latch mechanism portion of FIG. 6A with the latch mechanism in the intermediate non-blocking position.

In alternative embodiments, the ramp 190 is outwardly extending/facing from/on an extension (e.g., extending from the housing 12) such that it contacts the inner face 134 of the resilient finger 130 and deflects outwardly (away from the latch member) from its neutral state to its charged state, as depicted in FIGS. 6A-6B, respectively. In such embodiments, the pivot point 107 can be located on the extension defining the ramp 190. In still other embodiments, friction between a feature on the housing 12 or other portion of device 10 and the resilient finger 130 may be used to hold the latch member 102 in the blocking or intermediate non-blocking position, or the ramp 190 is eliminated and the latch member is urged to the blocking and intermediate non-blocking positions by gravity or other spring-biased latch retaining mechanisms or elements.

Having described details of the structure of the latch mechanism 100, details of its operation will now be described with respect to FIGS. 1A-1F. In a normal (e.g., neutral) state (FIG. 1A, see also FIGS. 3A-3E), the latch member 102 is in the blocking (leg-down/foot-up) position with the leg 110 lowered and generally aligned with the axis of translation of the lancet carrier 18, the blocking foot 120 raised and generally upright relative to the leg, and the finger 130 (and/or the leg) resting on a rib or shelf 194 of the housing 12. As the charging actuator 31 is retracted (as indicated by the linear-motion arrow in FIG. 1B) or otherwise actuated, the latch-pivoting element 135 of the charging mechanism 30 slides rearwardly against the charge-pivot face 122 of the foot 120 of the latch member 102, pivoting it (e.g., counter-clockwise as indicated by the angular-motion arrow in FIG. 1B) about the pivot pin 107 (see also FIG. 4). Retraction of the charging actuator 31 also retracts the lancet carrier 18 and the drive mechanism 15 by contact between the charging element or shoulder 33 (of the internal component 37 of the charging mechanism 30) and lancet carrier (e.g., the spring retainer 80 mounted at the distal end of the lancet carrier). As the latch member 102 pivots further, the foot 120 is lowered into a substantially horizontal orientation and the leg 110 is raised to a substantially upright orientation until the latch member is in the intermediate non-blocking (foot-down/leg-up) position (FIG. 1C). Thus, the lancing device 10 is now in the charged state with the latch mechanism 100 in the intermediate non-blocking position.

As the latch member 102 pivots from the blocking position of FIG. 1A (see also FIGS. 3A-3E), through the pivoting motion of FIG. 1B, to the intermediate non-blocking position of FIG. 1C, the outer face 132 of the finger 130 is pivoted into contact with the front ramped portion 191 of the ramp 190 (e.g., extending inward from the housing 12) to deflect the finger inward (toward the leg 110). As the latch member 102 pivots further, the outer face 132 of the finger 130 moves past the tipping point 193 and onto the rear ramped portion 192 of the ramp 190. In typical embodiments such as that depicted, the biasing force of the deflected finger 130 against the rear ramped portion 192 urges the latch member 102 all the way to the intermediate non-blocking position even if it has not been pivoted all the way there by the engagement of the latch-pivoting element 135 and the foot 120. By the time the latch member 102 has pivoted to the intermediate non-blocking position of FIG. 1C, the finger 130 has cleared the ramp 190 and resiliently deflected back out to retain the latch member in place.

As shown in FIG. 1D, when the lancing device 10 is actuated by operation of the release mechanism 40, for example by depressing the release actuator 41 (as indicated by the vertical-motion arrow), the discharging of the drive spring 14 drives the lancet carrier 18 and the attached spring retainer 80 forward to propel the lancet carrier through the drive/forward portion of the lancing stroke (as indicated by the horizontal-motion arrow). As the spring retainer 80 translates forward, it passes over the lowered foot 120 of the latch member 102 until its latch-engaging surface 181 contacts and pushes drive-pivot face 111 of the leg 110, which causes the latch member to reverse rotate (e.g., clockwise as indicated by the angular-motion arrow in FIG. 1D), thereby lowering the leg 110 and raising the blocking foot 120. In this way, the latch member 102 is pivoted from the intermediate non-blocking position back toward the blocking position.

In typical embodiments, the lancet carrier 18 and lancet 20 come to their fully extended/forward lancing position before the spring retainer 80 has pivoted the latch member 102 all the way back to the blocking position to avoid imparting vibrations to the lancet while puncturing the skin, as shown in FIG. 1D. In the depicted embodiment, at this point the finger 130 remains deflected and engaged on the front ramped portion 191 of the ramp 190, biasing the latch member 102 toward the blocking position (see also FIG. 5). But the latch member 102 is restrained from completing its full pivotal movement and held in this press non-blocking position (between the intermediate non-blocking and blocking positions) because the pressed surface 282 of the lancet carrier (e.g., of the spring retainer 80 or another element of the lancet carrier or drive mechanism 15) interferes with pressing surface 125 of the foot 120 (e.g., the latch chamfered face). Thus, the spring retainer 80 has a length such that it does not clear the space above the foot 120 when the lancet carrier 18 and the lancet 20 come to their fully extended/forward lancing position (see FIG. 1D).

The return spring 16 then returns the lancet carrier 18 from the extended/forward position back through the return/reverse portion of the lancing stroke (as indicated by the linear-motion arrow of FIG. 1E) toward the normal (e.g., neutral) position, with the spring retainer 80 retracting over the blocking foot 120 in its press non-blocking position (FIG. 1E). Because the charging mechanism 30 is not again being actuated, its latch-pivoting element 135 is not retracted to push the latch member 102 back to the intermediate non-blocking position. So upon the spring retainer 80 clearing the foot 120, the latch member 102 is now free to pivot to the blocking position, and the charged finger 130 discharges against the front ramp surface 191 to return the latch member to its blocking (leg-down/foot-up) position of FIG. 1F (see also FIGS. 1A and 3A-3E). The upright-positioned foot 120 then blocks the spring retainer 80 from passing forward again under the force of the drive spring 14, thereby arresting any further/excess/secondary oscillation of the drive mechanism 15 and preventing the lancet tip 22 from subsequent advancement and potential re-contact with the lancing site.

In the depicted embodiment, there is also provided a lancet-ejection mechanism 60. When the endcap 50 of the lancing device 10 is installed on the housing 12, abutment of an extension 62 of the ejection mechanism 60 against the cap prevents actuation of the ejection mechanism. To eject the lancet, the cap 50 is removed to allow the ejection mechanism 60 to advance. When the extension 62 of the ejection mechanism 60 is advanced, an ejection finger 64 of the ejection mechanism contacts the lancet 20 through a slot in the lancet carrier 18 to eject the lancet from the lancet carrier in a forward direction (see FIG. 1F). Contact by the foot 120 of the latch member 102 against the spring retainer 80 prevents forward motion of the lancet carrier 18 during ejection of the lancet, enabling a shorter ejection stroke. In other embodiments, the ejection mechanism is eliminated (i.e., for disposable lancing devices) or provided in another conventional form.

FIGS. 7A-11C show the lancing device 10 as substantially described above, except including a latch mechanism 200 according to a second example embodiment of the present invention. The latch mechanism 200 includes a latch member 202, a spring-biased latch retainer 290, a latch-pivoting element 235 of the charging mechanism 30, and a latch-engaging element 281, a pressed surface 282, and a blocking surface 283 of the lancet carrier 18, that cooperatively function to produce a substantially similar result to that of the first embodiment. That is, a first forward and rearward oscillation of the lancet 20 is permitted when the latch member 202 is in intermediate and press non-blocking positions, and subsequent/excess/secondary oscillations are prevented when the latch mechanism is in a blocking position. The latch member 202 pivots (rotates) between the blocking and non-blocking positions about an axis B (FIG. 7C) that is parallel (e.g., coaxial) with the linear advancement and retraction motion of the lancet carrier 18 during the lancing stroke.

Figure 7A:
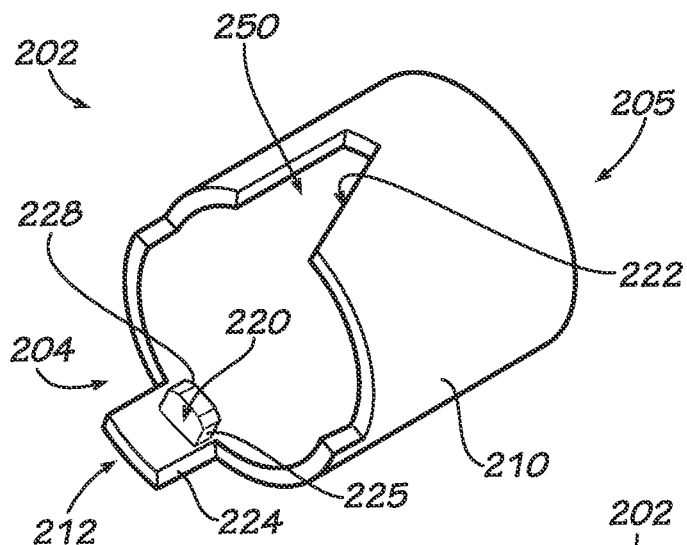
FIG. 7A is a front perspective view of a latch member of a latch mechanism of a lancing device according to a second example embodiment of the present invention.
Figure 7B:
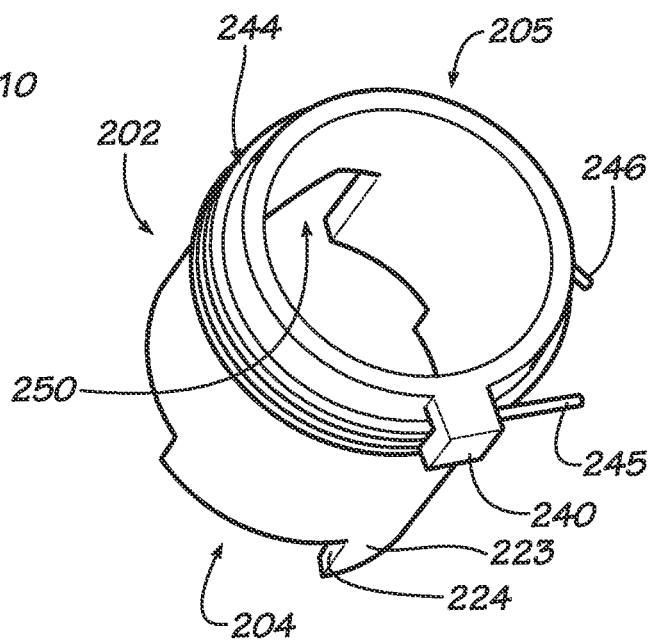
FIG. 7B is a rear perspective view of the latch member of FIG. 7A, showing a torsion spring coupled thereto.
Figure 7C:
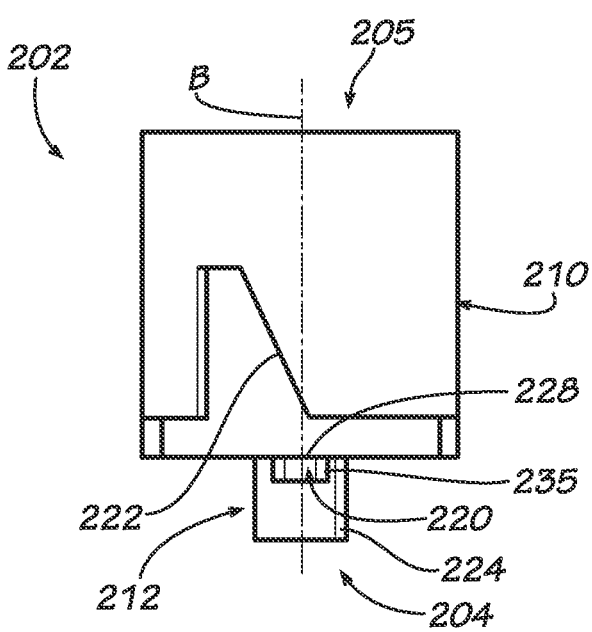
FIG. 7C is a top view of the latch member of FIG. 7A.

FIGS. 7A-7C show details of the sleeve latch member 202. The latch member 202 is typically in the form of a cylindrical or tubular sleeve that pivots (rotates) about an axis, though it can be in the form of a curved wall section that does not define a complete circle/cylinder. The latch member 202 includes a sleeve body 210 extending from a first end 204 to a second end 205 and defining a retainer-biasing surface 223, an anti-pivot surface 224, a pressing surface 225, a drive-stop surface 228, and a charge-pivot cam surface 222. In addition, the latch member 202 includes a spring 244 that pivotally (i.e., rotationally) biases it in an angular direction.

The anti-pivot surface 224 is formed on an axial/radial side of the sleeve body 210 and engages the spring-biased latch retainer 290. In the depicted embodiment, for example, the sleeve body 210 includes a tooth (e.g., a tab, wedge, post, or other projection) 212 that is integrally formed with or attached to it and that has at least a portion extending generally axially therefrom, with the anti-pivot surface 224 formed on an axial/radial side of the tooth. The anti-pivot surface 224 of the tooth 212 is angled (with respect to a radius line) or otherwise formed to accommodate interaction with the spring-biased latch retainer 290. Thus, the anti-pivot surface 224 can be angled so that when the sleeve body 210 is pivoted into the non-blocking position, it is flush with the catch surface 295 of the spring biased latch retainer 290.

The retainer-biasing surface 223 is formed on the sleeve body 210 and engages the spring-biased latch retainer 290. In the depicted embodiment, for example, the sleeve body 210 includes the tooth 212, and the retainer-biasing surface 223 is formed on the outer surface of the tooth of the sleeve body. The spring-biased latch retainer 290 contacts the retainer-biasing surface 223 when the latch member 202 is in the blocking position and the spring-biased latch retainer is in the charged position, with this contact retaining the latch retainer in the charged position (see FIGS. 9A, 10A, and 11A).

The pressing surface 225 is formed on an axial/radial side of the sleeve body 210 and engages the pressed surface 282 of the lancet carrier 18. And the drive-stop surface 228 is formed on the rear side (transverse to the axial/radial side) of the sleeve body 210 and engages the latch-engaging surface 281 of the lancet carrier 18. In the depicted embodiment, for example, the sleeve body 210 includes a foot (e.g., a tooth, tab, post, wedge, or other projection) 220 that is integrally formed with or attached to it and that extends generally transversely and radially inward therefrom (e.g., from the tooth 212 or adjacent the tooth), with the pressing surface 225 formed on an axial/radial side of the foot and the drive-stop surface 228 is formed on the rear side of the foot. The pressing surface 225 provides a sufficient contact surface for interference engagement with the pressed surface 282 of the lancet carrier 18 when the latch member 202 is in the press non-blocking angular position (see FIGS. 7C, 9C, 10C, and 11C).

The charge-pivot surface 222 is formed on an axial/radial surface (transverse to the front and rear sides) of the sleeve body 210 and engages the latch-pivoting element 235 of the charging mechanism 30. In the depicted embodiment, for example, the sleeve body 210 includes a void 250 formed near the first end 204 of the latch member 202, with the charge-pivot surface 222 defining a portion of the void. The charge-pivot surface 222 is angled with respect to the axis of the sleeve body 210 so that when the latch-pivoting element 235 of the charging mechanism 30 is moved longitudinally along it the latch member 212 pivots in an angular direction from the blocking position to the intermediate non-blocking position. In alternative embodiments, the charge-pivot surface 222 is formed on a wedge extending radially outward from the sleeve body 210, is non-linear to provide for a non-constant pivoting rate, is non-angled (or less angled) with the latch-pivoting element 235 being angled, or is provided in other configurations for providing the functionality described herein.

The latch spring 244 biases the latch member 202 to pivot from the intermediate and press non-blocking positions toward the blocking position. In the depicted embodiment, the latch spring 244 is a torsion spring that is positioned around the sleeve body 210 and mounted to it by a retaining bracket 240 at the second end 205 of the latch member 202. For example, a first arm 245 of the torsion spring can be retained by the retaining bracket 240 and a second arm 246 can engage the housing 12 or another part of the lancing device 10. In other embodiments, the latch spring is a compression or tension coil spring, a leaf spring, a resiliently deformable member, or another type of spring element that biases the latch member 202 as described herein.

The latch-pivoting element 235 of the charging mechanism 30 engages the charge-pivot cam surface 222 and thereby pivots the latch member from the blocking position to the intermediate non-blocking position when the charging actuator 31 is operated to charge the drive mechanism 15. In the depicted embodiment, for example, the latch-pivoting element 235 is a pin that extends radially inward from an internal component of the charging mechanism 30 and slides along the charge-pivot surface 222. In other embodiments, the latch-pivoting element is a post, bar, rod, shaft, panel, finger, boss, or another element that engages the charge-pivot cam surface to pivot the latch member 202 as described herein.

The latch-engaging element 281 and the blocking surface 283 of the lancet carrier 18 engage the spring-biased latch retainer 290, and the pressed surface 282 of the lancet carrier 18 is engaged by the pressing surface 225 of the latch 202. In the depicted embodiment, for example, the latch-engaging element 281, the pressed surface 282, and the blocking surface 283 are contact surfaces formed on forward, lateral, and bottom faces of a spring retainer 80 of the lancet carrier 18, with the spring retainer retaining the return spring 16 in place on the lancet carrier for charging and discharging. In other embodiments, these surfaces are defined by one, two, or three other elements of the lancet carrier 18, whether dedicated element for use only in the latch mechanism or for shared use in other functions of the lancing device.

Figure 8A:
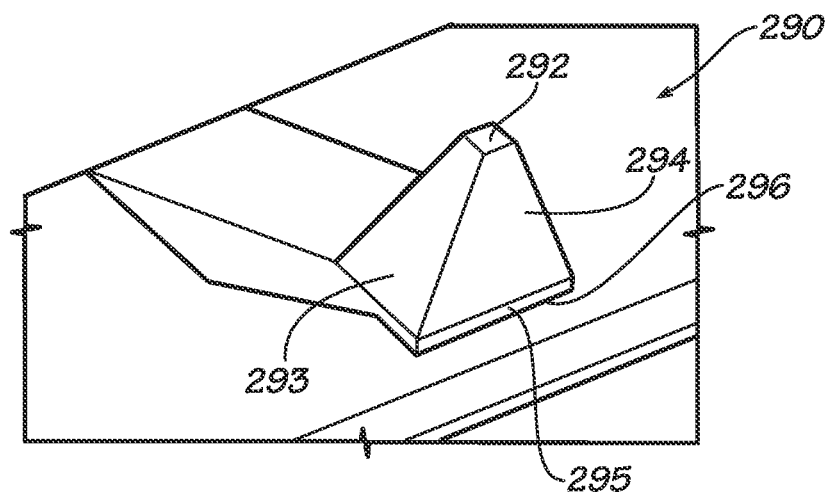
FIG. 8A is a rear perspective view of a spring finger of the latch mechanism of FIGS. 7A-7C.
Figure 8B:
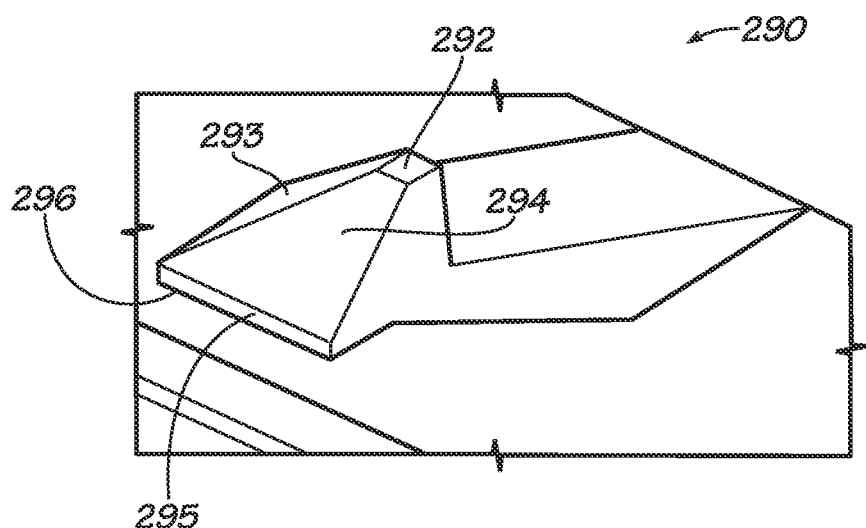
FIG. 8B is a front perspective view of the spring finger of FIG. 8A.

FIGS. 8A-8B show details of the spring-biased latch retainer 290 of the depicted embodiment, which is in the form of a resilient finger that is biased from a charged non-latch-retaining position to a discharged latch-retaining position. The resilient finger 290 extends from a stationary element of the lancing device 10 and includes contact surfaces that selectively engage the latch member 202 and the lancet carrier (or an element coupled thereto) 18 to provide for permitting a first lancet oscillation and preventing subsequent oscillations. In the depicted embodiment, for example, the resilient finger 290 is a cantilevered arm with a head at its free end, the arm projecting inwardly from the housing 12 and the head defining the contact surfaces for engaging the latch member 202 and the lancet carrier 18. The contact surfaces of the resilient finger 290 include a first surface 292, second surface 293, third surface 294, and fourth surface 295.

Figure 9A:
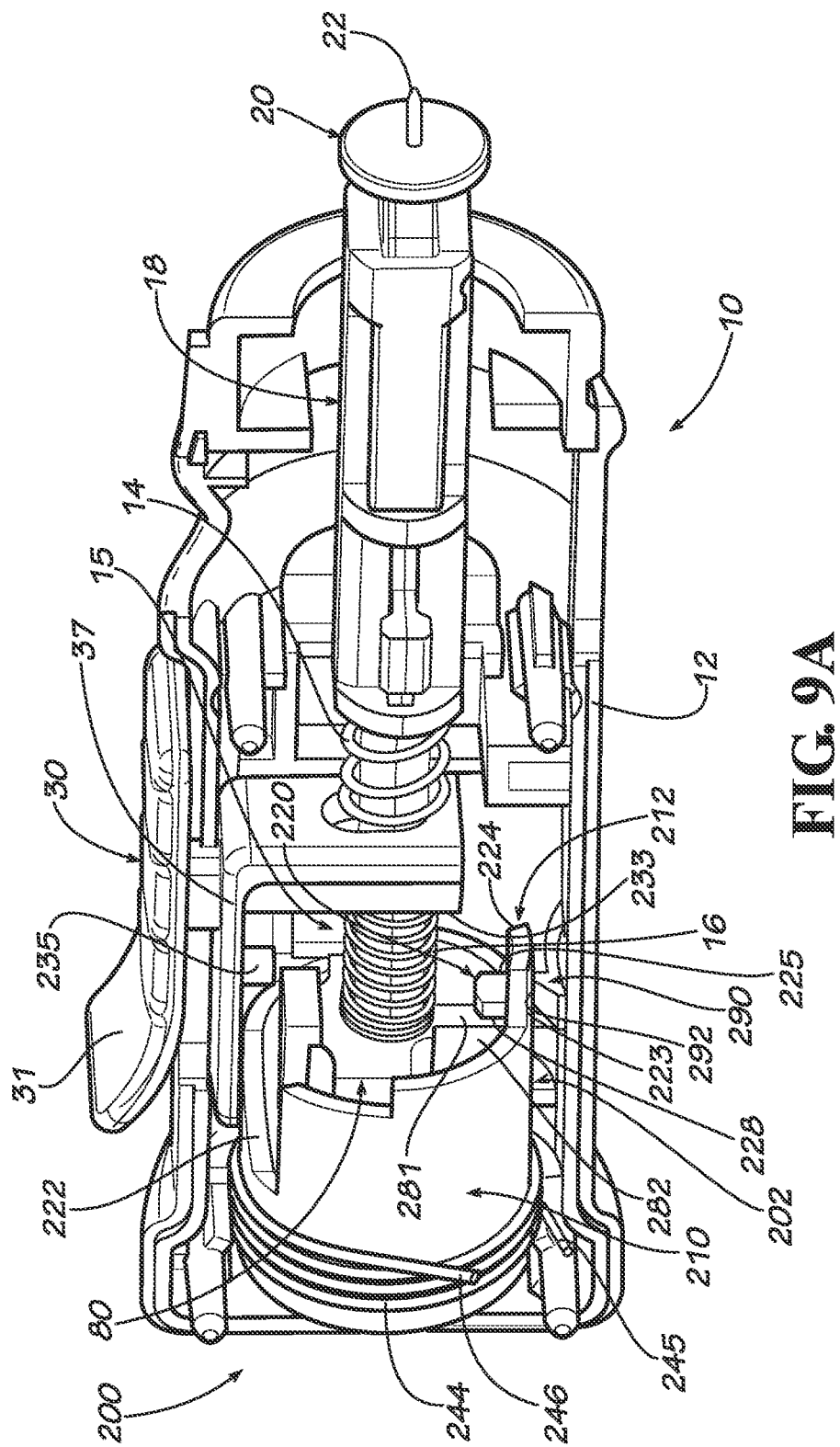
FIG. 9A is a perspective view of the lancing device with the latch mechanism of FIGS. 7A-8B, with portions removed to show internal components thereof, showing the latch in a blocking position.
Figure 9C:
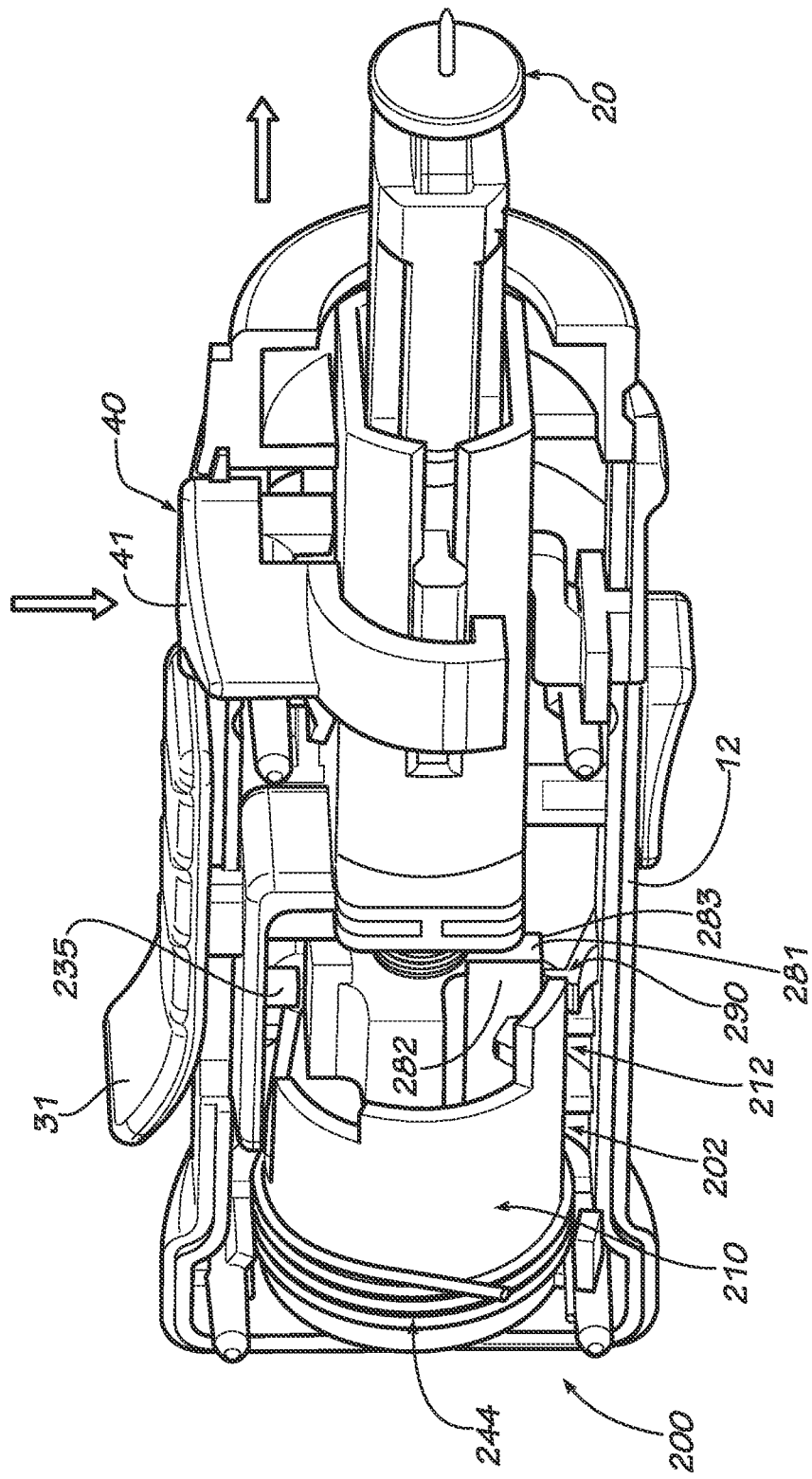
FIG. 9C shows the lancing device of FIG. 9B with the lancet traveling along a forward portion of its lancing stroke and the latch pivoted to a press non-blocking position.
Figure 10A:
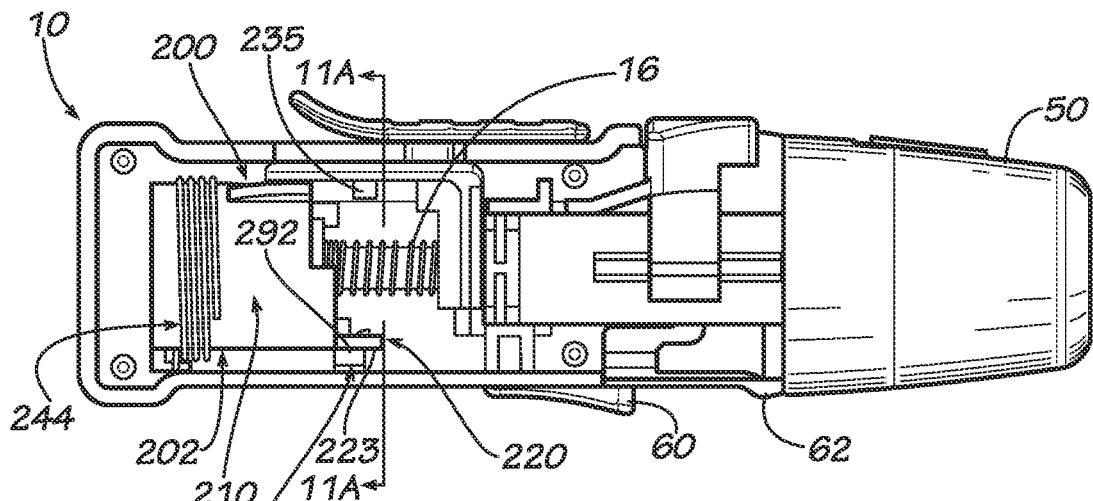
FIG. 10A is a side view of the lancing device in the blocking position of FIG. 9A.
Figure 10C:
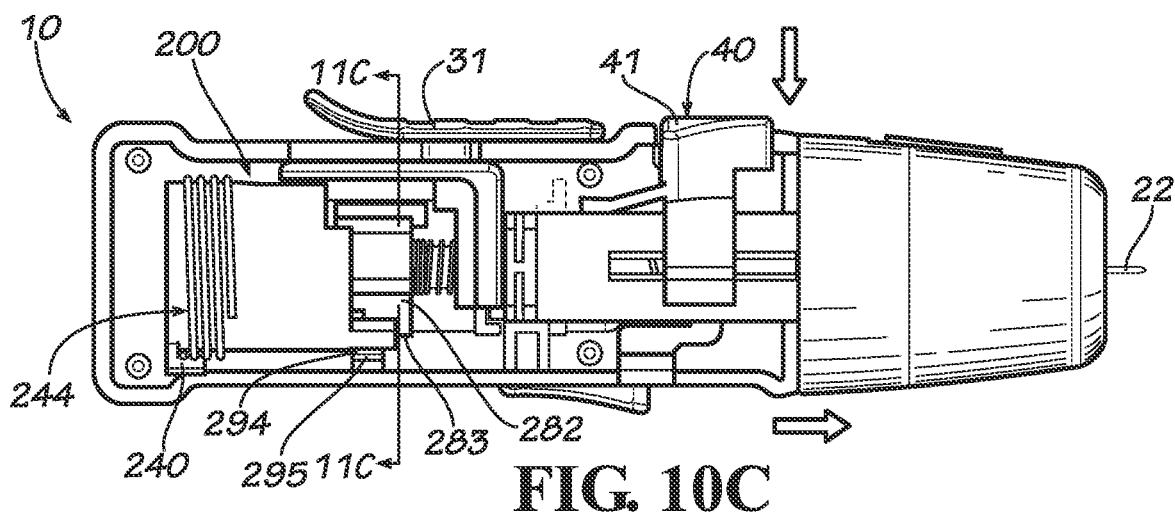
FIG. 10C is a side view of the lancing device in the press non-blocking position of FIG. 9C.
Figure 11A:
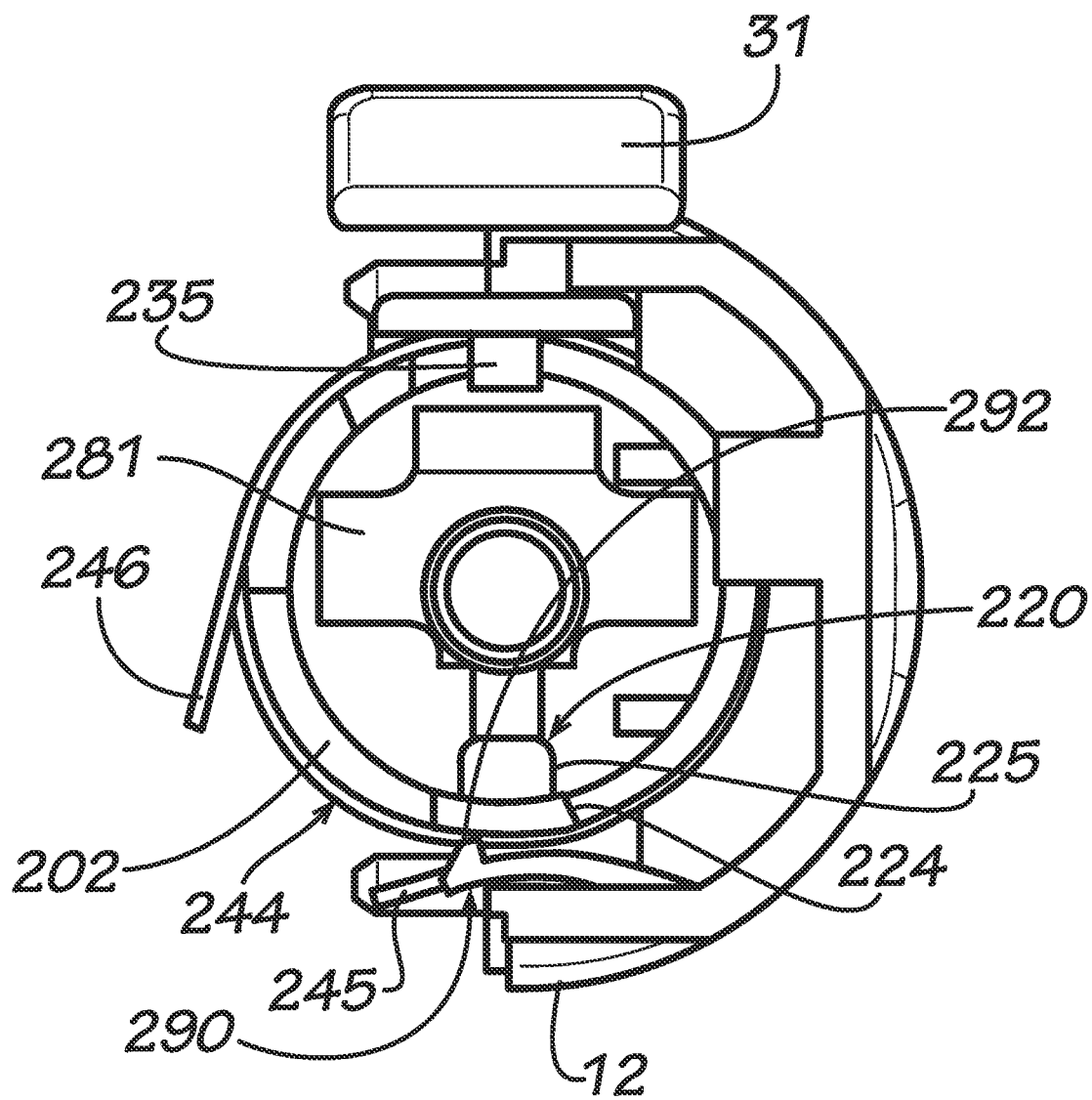
FIG. 11A is a cross-sectional view of the lancing device taken at line 11A-11A of FIG. 10A.

The first surface 292 contacts the latch member 202, for example the retainer-biasing surface 223 of the tooth 212 of the sleeve body 210, when the latch member is in the blocking position and the resilient finger 290 is in the charged non-latch-retaining position, with this contact retaining the resilient finger in position (see FIGS. 9A, 10A, and 11A). The first surface 292 can also contact the lancet carrier 18, for example the blocking surface 283 of the spring retainer 80, when the latch member is in the press non-blocking position and the resilient finger 290 is in the partially charged (e.g., deflected) non-latch-retaining position, with this contact retaining the resilient finger in position (see FIGS. 9C, 10C, and 11C).

Figure 9B:
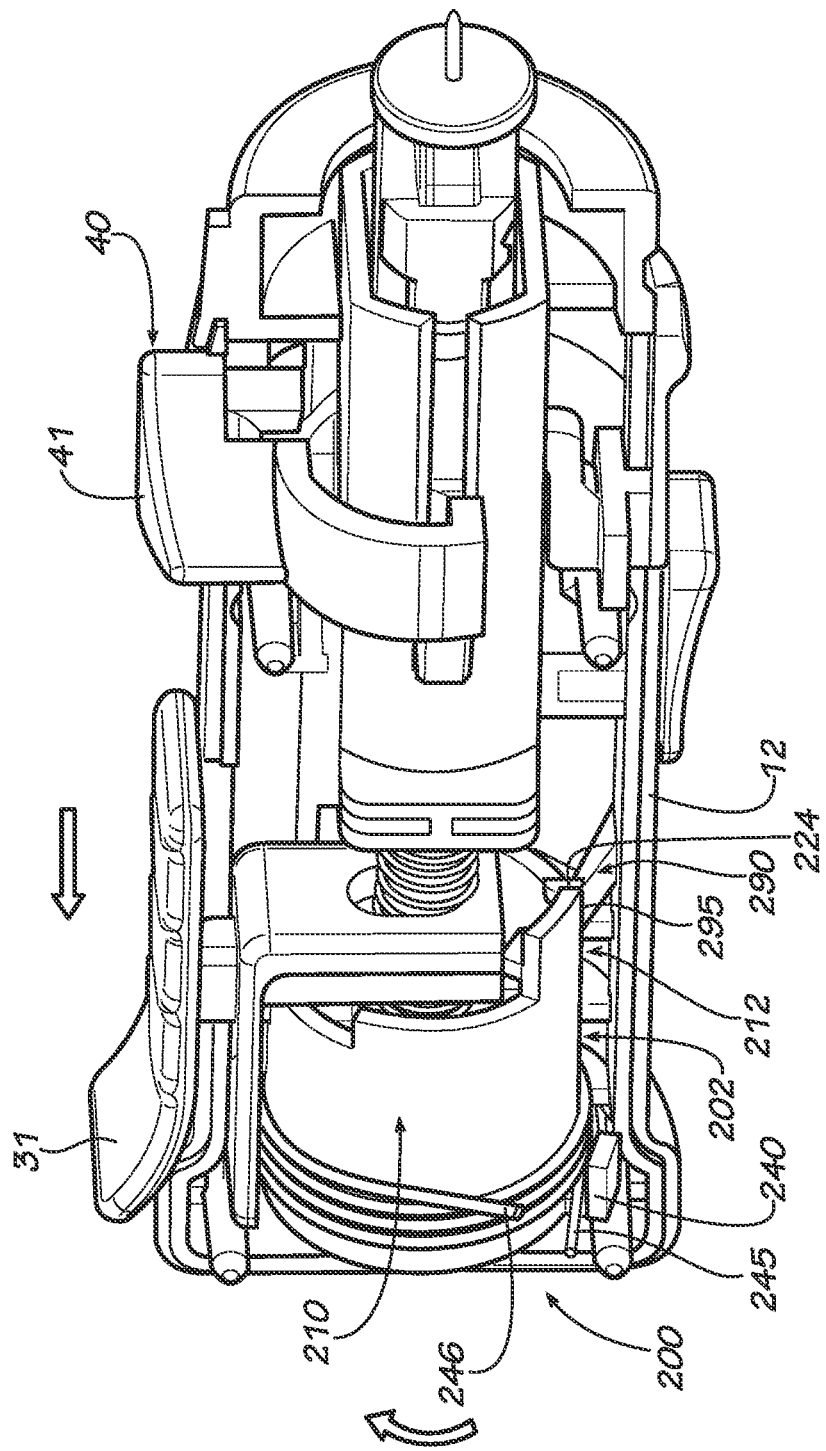
FIG. 9B shows the lancing device of FIG. 9A with the drive mechanism being charged and the latch pivoted to an intermediate non-blocking position.
Figure 10B:
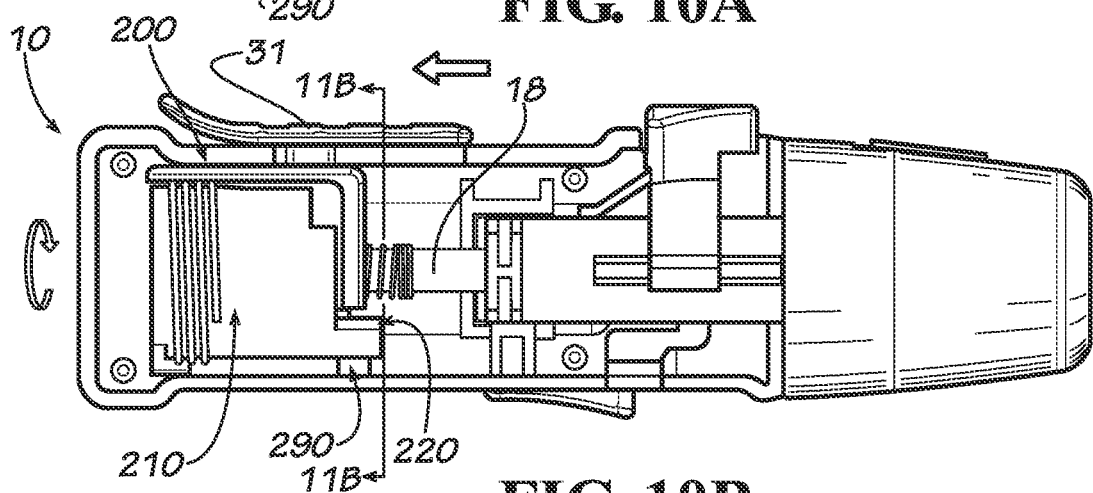
FIG. 10B is a side view of the lancing device in the intermediate non-blocking position of FIG. 9B.
Figure 11B:
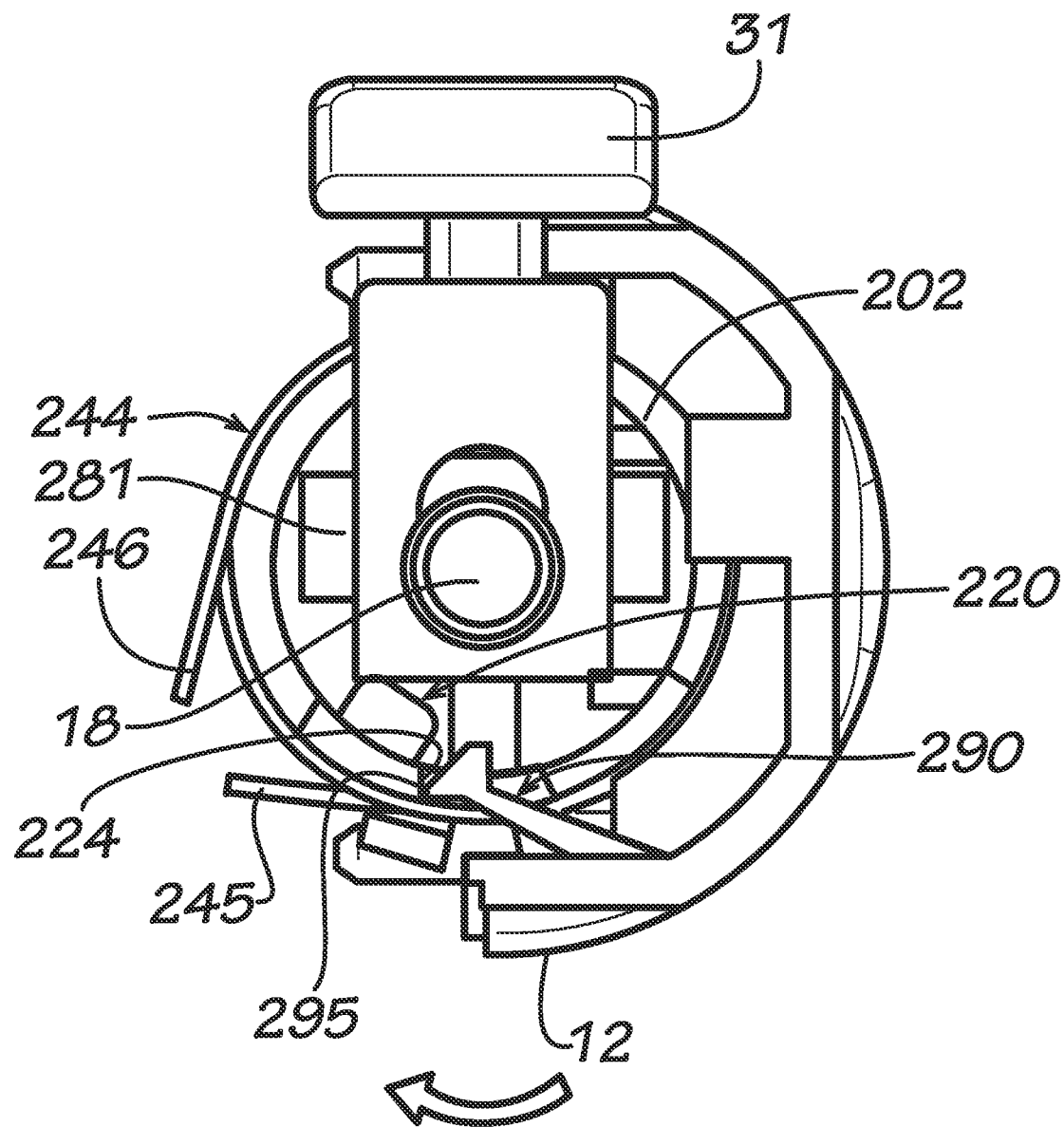
FIG. 11B is a cross-sectional view of the lancing device taken at line 11B-11B of FIG. 10B.

The fourth surface 295 contacts the latch member 202, for example the anti-pivot surface 224, when the latch member is in the intermediate non-blocking position and the resilient finger 290 is in the discharged latch-retaining position, with this contact retaining the latch member in the intermediate non-blocking position (see FIGS. 9B, 10B, and 11B).

Figure 11C:
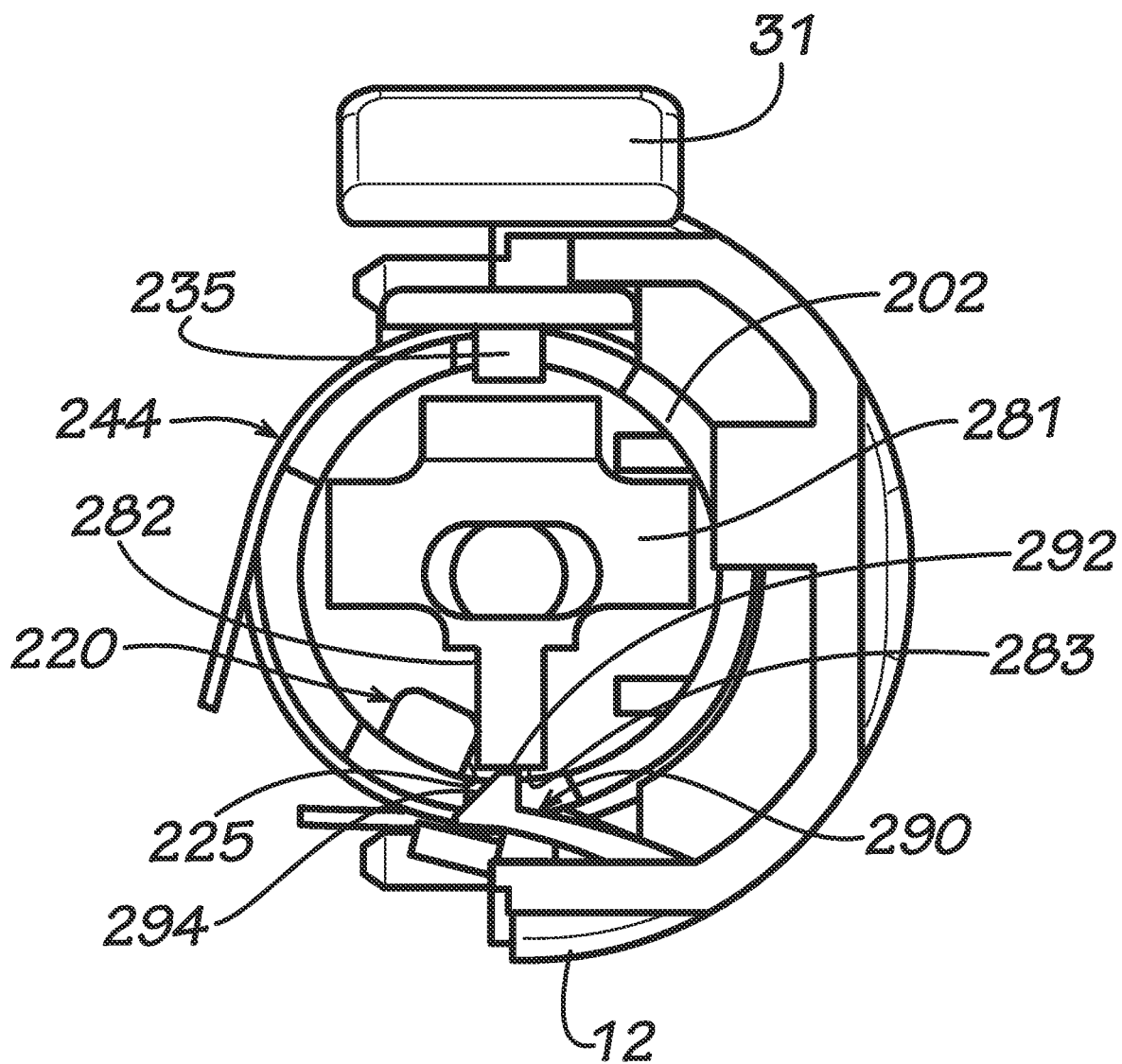
FIG. 11C is a cross-sectional view of the lancing device taken at line 11C-11C of FIG. 10C.

The third surface 294 extends between the first and fourth surfaces 292 and 295 and is ramped (e.g., chamfered or beveled) to facilitate smooth movement across the anti-pivot surface 224 (or portions thereof) when the resilient finger 290 is in partially charged positions moving between the charged non-latch-retaining and discharged latch-retaining positions (see FIGS. 9C, 10C, and 11C).

And the second surface 293 contacts the lancet carrier 18, for example the latch-engaging surface 281, and is ramped (e.g., chamfered or beveled) so that when the lancet carrier is being propelled forward through the lancing stroke the latch-engaging surface 281 of the lancet carrier rides along the ramped second surface 293 to deflect the resilient finger 290 and thereby withdraw it from the discharged latch-retaining position toward the charged non-latch-retaining position (in positions between the positions of FIGS. 11B and 11C).

Typically, but not necessary in all commercial embodiments, the resilient finger 290 is fully discharged in the discharged position (that is, in some embodiments the resilient finger can still have a small charge when in the "discharged" position). In other embodiments, instead of the cantilevered resilient finger, the spring-biased latch retainer includes a compression or tension coil spring, a torsion spring, a leaf spring, a resiliently deformable member, or another type of spring element, and still includes the contact surfaces that biasingly engage the lancet carrier 18 and the latch member 202 to provide the functionality described herein. In still other embodiments, the latch retainer is not spring-biased and instead is moved between the non-latch-engaging and latch-engaging positions by an additional mechanism or element. And in yet still other embodiments, the latch retainer is eliminated or formed by an element of the charging mechanism 30 so that the charging mechanism temporarily retains the latch 202 in the intermediate position until the lancet carrier 18 moves far-enough forward that the latch member can be released to reverse-pivot to the press non-blocking position.

FIGS. 9A-9C, 10A-10C, and 11A-11C show the operational use of the latch mechanism 200. In a normal (e.g., neutral) state (FIGS. 9A, 10A, and 11A), the latch member 202 is in the blocking position with the foot 220 inserted into the lancing stroke path of the lancet carrier 18 (and/or the lancet 20). In use, as the charging actuator 31 is retracted (as indicated by the linear-motion arrow in FIGS. 9B and 10B) or otherwise actuated, the latch-pivoting element 235 of the charging mechanism 30 slides rearwardly against the ramped charge-pivot cam face 222 of the latch member 202, pivoting the latch member (e.g., as indicated by the angular-motion arrow in FIGS. 9B and 10B) about its axis (e.g., the lancing path axis) from its blocking position to its non-blocking position of FIGS. 9B, 10B, and 11B. Retraction of the charging actuator 31 also retracts the lancet carrier 18 and the drive mechanism 15 by contact between the charging element or rib 33 (of an internal component 37 of the charging mechanism 30) and the lancet carrier (e.g., the spring retainer 80 mounted at the distal end of the lancet carrier). As the latch member 202 pivots from its blocking position to its intermediate non-blocking position, the spring 244 begins to transition from a normal (neutral/uncharged or only slightly charged) state to a charged state to bias the latch member 202 back towards the blocking position. In the depicted embodiment, for example, as the latch member 202 rotates, the retaining bracket 240 follows along the spring first arm 245, and as a result the spring second arm 246 is engaged with an inner portion (e.g., an inner wall surface) of the housing 12 (or another element of the lancing device 10), thus charging the torsional spring to bias the latch member 202 towards the blocking position. The lancing device 10 is now in the charged state with the latch mechanism 200 retained in the intermediate non-blocking position.

The pivotal movement of the latch mechanism 202 from the blocking position to intermediate non-blocking position frees the spring-biased latch retainer 290 (e.g., the resilient finger) to move from the charged non-latch-retaining position to the discharged latch-retaining position. For example, when the latch member 202 is in the blocking position, the resilient finger 290 can be deflected outward with the first finger surface 292 biased against the retainer-biasing surface 223 of the latch body 210. In the particular case of the depicted embodiment, when the latch member 202 is in the blocking position, the first finger surface 292 is positioned below the tooth 212 and the finger-blocking surface 223 is defined by the outer wall of the tooth of the latch body 210 (FIGS. 9A, 10A, and 11A). And when the latch member 202 is pivoted to the intermediate non-blocking position, the retainer-biasing surface 223 of the latch 202 is pivoted out of contact with the resilient finger 290 (FIGS. 9B, 10B, and 11B). So the charged resilient finger 290, now free of the interference with the latch member 202, discharges and thereby deflects inward from the charged position to the discharged position.

In the discharged latch-retaining position, the resilient finger 290 prevents the latch member 200 in the intermediate non-blocking position from reverse pivoting back toward the blocking position. In the depicted embodiment, for example, the fourth finger surface 295 (or adjacent surfaces/edges) aligns with the anti-pivot surface 224 of the tooth 212 of the latch member 202 in an interference position to prevent such reverse pivoting (FIGS. 9B, 10B, and 11B).

To initiate the lancing stroke, the release mechanism 40 is actuated to release the lancet carrier 18 to be propelled through the lancing stroke by the drive mechanism 15. In the depicted embodiment, for example, the release actuator 41 is depressed (as indicated by the downward linear arrow of FIGS. 9C and 10C) to disengage mating elements of the release mechanism 40 and the lancet carrier 18. The released lancet carrier 18 is then propelled along the forward portion of the lancing stroke by the discharging drive spring 14.

As the lancet carrier 18 moves forward, a portion of it engages the resilient finger 290 and displaces it out of the way. In the depicted embodiment, the blocking surface 283 of the lancet carrier 18 (e.g., formed on the lancet carrier's spring retainer 80) comes into contact with the second finger surface 293. The second finger surface 293 is ramped (and/or the blocking surface 283 can be ramped) so that this engagement deflects the resilient finger 290 from the discharged latch-retaining position to a partially charged non-latch-retaining position (FIGS. 9C, 10C, and 11C). So now the fourth finger surface 295 has been removed from interference/alignment with the anti-pivot surface 224 of the latch member 202, and the latch member reverse-pivots (in the second/reverse angular direction) slightly under the biasing force of the charged spring 244 to the press non-blocking position. But because the lancet carrier 18 has moved forward, its pressed surface 282 (e.g., of the spring retainer 80) is now in an interfering position with (and is thus pressed upon by) the pressing surface 225 (e.g., of the foot 220) of the spring-biased latch member 202 to block the latch member from further reverse-pivoting (FIGS. 9C, 10C, and 11C).

The lancet carrier 18 continues blocking the latch member 202 from further reverse-pivoting as it travels forward to the fully extended position to lance the subject's skin and then begins retracting on the reverse portion of the lancing stroke. Thus, the pressed surface 282 of the lancet carrier 18 has a length sufficient to maintain this interference with the pressing surface 225 of the latch member 202 during these segments of the forward and reverse portions of the lancing stroke. Friction caused by contact between the pressed surface 282 (e.g., of the spring retainer 80) and the pressing surface 225 (e.g., of the foot 220) is substantially small so that the lancing movement is smooth and easy.

Once the lancet carrier 18 retracts to where its pressed surface 282 has cleared blocking interference with the pressing surface 225 of the latch member 202, the latch member then further reverse-pivots (in the second/reverse angular direction), under the biasing force of the charged spring 244, back to the blocking position of FIGS. 9A, 10A, and 11A. This in turn causes the anti-pivot surface 224 of the latch member 202 to drive against the ramped third surface 294 of the resilient finger 290 to return/deflect the finger to the charged non-latch-retaining position.

After this first lancet oscillation (i.e., the lancing stroke), the drive spring 14 may be sufficiently re-charged to initiate a subsequent lancet oscillation. But with the latch member 202 in the blocking position of FIGS. 9A, 10A, and 11A, the blocking drive-stop surface 228 of the latch member 202 (e.g., of its tooth 220) is now in an interference position (inserted into the path of the lancet carrier 18 and/or the lancet 20) so that it will contact the latch-engaging surface 281 of the lancet carrier (e.g., of its spring retainer 80) and block it from further forward travel. In this way, excess oscillations of the lancet 20 are prevented, thereby minimizing the pain associated with repeated sticks by the lancet tip 22.

In alternative embodiments, the latch mechanism does not include the spring finger 290 (or the surfaces of the latch and other mechanisms of the lancing device that it engages) and instead includes other types of spring-biased latch retainers that retain the latch member in the intermediate non-blocking position but only until the portion of the lancet carrier that the latch presses against moves into an interference position during the forward portion of the lancing stroke. In some such embodiments, the spring-biased latch retainer is a spring-biased plunger (e.g., a spring-biased pin or projection) extending from the latch member (or the housing) for operating similarly to the resilient finger 290. In one embodiment, for example, the plunger extends axially from the second end of the latch where it is biased against a portion of the housing. During charging, the spring-biased plunger rides along the housing as the latch member pivots until it aligns with an anti-pivot pocket (e.g., formed with the housing) in the intermediate non-blocking position, and then the plunger is extended into the pocket under the biasing influence of its spring force, thereby retaining the latch member in the intermediate non-blocking position. As the lancet carrier travels forward after operation of the actuation mechanism, a plunger-retraction member (e.g., of the lancet carrier) is engaged to retract the plunger from the anti-pivot pocket and the latch member reverse-pivots slightly (in the second angular direction) under the biasing force of the charged spring to the press non-blocking position. From there, the operation of the latch mechanism is the same as described above. It will be understood that included within the scope of the invention are other forms of spring or biasing latch-retaining elements that operate to retain the latch member in the intermediate non-blocking position and then release the latch member to reverse-pivot to the press non-blocking position as a part of the overall operation to permit the first forward and rearward oscillation of the lancet and to then prevent subsequent/excess oscillations after the latch member returns to the blocking position.

In the depicted embodiment, the latch member 202 pivots in a first angular direction (counter-clockwise when viewed from behind) and a second opposite angular direction (clockwise when viewed from behind) when functioning to permit the first oscillation of the lancet 20 and prevent subsequent oscillations. In other embodiments, the latch mechanism is configured so that the latch member pivots in opposite directions or pivots in only one angular direction (whether clockwise or counter-clockwise) when functioning to permit the first oscillation of the lancet and prevent subsequent oscillations.

While the invention has been described with reference to preferred and example embodiments, it will be understood by those skilled in the art that a variety of modifications, additions and deletions are within the scope of the invention, as defined by the following claims.

What is claimed is:

1. A lancing device for use with a disposable lancet having a lancet body and a sharp lancet tip for penetrating skin, comprising:
    a housing defining a cavity;
    a lancet carrier positioned within the cavity, the lancet carrier being configured to releasably engage a disposable lancet, the lancet carrier being movable in a direction along a lancing stroke from a retracted position to an extended position where at least the sharp lancet tip of the disposable lancet is configured to project out from the housing;
    a return spring positioned within the cavity and configured to propel the lancet carrier from the extended position to a neutral position;
    a drive spring positioned within the cavity and configured to propel the lancet carrier from the retracted position to the extended position;
    a removable cap positionable over a distal end of the housing, wherein removal of the cap from the housing allows access to the cavity in order to remove and replace the disposable lancet; and
    an ejection member having an ejection finger and an extension, the ejection member being movable distally to eject the disposable lancet from the lancet carrier, wherein the extension extends longitudinally and wherein at least a portion of the ejection finger is laterally offset relative to the extension and wherein the offset portion of the ejection finger is parallel to the extension.

2. The lancing device of claim 1, wherein the ejection finger is configured to eject the disposable lancet when the ejection member moves distally.

3. The lancing device of claim 2, wherein the extension bears against the removable cap when the cap is positioned over the distal end of the housing.

4. The lancing device of claim 3, wherein the ejection finger of the ejection member comprises a portion that extends generally along the direction of the lancing stroke and a portion that extends generally in a direction perpendicular to the direction of the lancing stroke.

5. The lancing device of claim 3, wherein the ejection finger of the ejection member has a surface defining a plane perpendicular to the direction of the lancing stroke.

6. The lancing device of claim 1, wherein the ejection finger and extension are unitary with the ejection member.

7. The lancing device of claim 1, wherein the ejection member is moveable separately from the lancet carrier.

8. A lancing device for use with a disposable lancet having a lancet body and a sharp lancet tip for penetrating skin, comprising:
    a housing defining a cavity;
    a lancet carrier positioned within the cavity, the lancet carrier having a slot and being configured to releasably engage a disposable lancet, the lancet carrier being movable in a direction along a lancing stroke from a retracted position to an extended position where at least the sharp lancet tip of the disposable lancet is configured to project out from the housing;
    a return spring positioned within the cavity and configured to propel the lancet carrier from the extended position to a neutral position;
    a drive spring positioned within the cavity and configured to propel the lancet carrier from the retracted position to the extended position;

a removable cap positionable over a distal end of the housing, wherein removal of the cap from the housing allows access to the cavity in order to remove and replace the disposable lancet;

an ejection member having an ejection finger and an extension, the ejection finger extending through the slot to contact the disposable lancet and the ejection member being movable distally to eject the disposable lancet from the lancet carrier, the extension extending along the direction of the lancing stroke distally beyond the ejection finger, wherein a portion of the ejection finger extends longitudinally and is laterally offset relative to the extension; and a button operably connected to the lancet carrier and configured to hold the lancet carrier in the retracted position and, when pressed, to release the lancet carrier and to allow the lancet carrier to move from the retracted position to the extended position.

9. The lancing device of claim 8, further comprising a slide operably connected to the lancet carrier and adapted to move the lancet carrier from the neutral position to the retracted position to energize the drive spring.

10. The lancing device of claim 8, wherein the ejection member is moveable separately from the lancet carrier.

11. The lancing device of claim 8, wherein the ejection finger and extension are unitary with the ejection member.

12. The lancing device of claim 11, wherein the ejection finger of the ejection member has a surface defining a plane perpendicular to the direction of the lancing stroke.

* * * * *